US012622885B2

(12) United States Patent

Schafmeister et al.

(10) Patent No.: US 12,622,885 B2
(45) Date of Patent: May 12, 2026

(54) SHORT CHAIN FATTY ACID COMPOUNDS AND USES THEREOF

(71) Applicant: Temple University-Of The Commonwealth System of Higher Education, Philadelphia, PA (US)

(72) Inventors: Christian Schafmeister, Philadelphia, PA (US); Alla Arzumanyan, Huntington Valley, PA (US); Ira C. Spector, Jenkintown, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 19/207,954

(22) Filed: May 14, 2025

(65) Prior Publication Data

US 2025/0268851 A1 Aug. 28, 2025

Related U.S. Application Data

(63) Continuation of application No. PCT/US2024/061643, filed on Dec. 23, 2024.

(60) Provisional application No. 63/614,077, filed on Dec. 22, 2023.

(51) Int. Cl.

| | |
|---|---|
| *A61K 31/19* | (2006.01) |
| *A61K 9/00* | (2006.01) |
| *A61K 9/20* | (2006.01) |
| *A61K 9/48* | (2006.01) |
| *A61K 31/59* | (2006.01) |
| *A61K 33/06* | (2006.01) |
| *A61P 17/06* | (2006.01) |

(52) U.S. Cl.
CPC ............ *A61K 31/19* (2013.01); *A61K 9/0053* (2013.01); *A61K 9/20* (2013.01); *A61K 9/48* (2013.01); *A61K 31/59* (2013.01); *A61K 33/06* (2013.01); *A61P 17/06* (2018.01)

(58) Field of Classification Search
CPC ........ A61K 31/19; A61K 9/0053; A61K 9/20; A61K 33/06; A61K 31/593
See application file for complete search history.

(56) References Cited

U.S. PATENT DOCUMENTS

| | | | |
|---|---|---|---|
| 2018/0161292 A1* | 6/2018 | Kuang | A23L 33/40 |
| 2021/0403407 A1 | 12/2021 | Tung | |

FOREIGN PATENT DOCUMENTS

| | | |
|---|---|---|
| WO | 2016118730 | 7/2016 |
| WO | 2018140687 | 8/2018 |
| WO | 2022031787 | 2/2022 |
| WO | 2022104116 | 5/2022 |
| WO | 2024102902 | 5/2024 |
| WO | 2024151503 | 7/2024 |

OTHER PUBLICATIONS

Jardet C, et al. "Development and characterization of a human Th17-driven ex vivo skin inflammation model," Exp Dermatol, 2020, 29(10):993-1003.
Soldatic K. "Development of an LC-MS/MS method for the assessment of the effect of spinal cord injury on dysbiosis and short-chain fatty acid quantity in rats", University of Rijeka, Jun. 2023: 1-68.

* cited by examiner

Primary Examiner — Deborah D Carr

(74) Attorney, Agent, or Firm — Riverside Law LLP

(57) ABSTRACT

The present disclosure describes compositions comprising at least one short chain fatty acid (SCFA). The present disclosure describes compositions comprising at least one SCFA wherein one or more hydrogen atoms in the SCFA or the pharmaceutically-acceptable salt thereof is isotopically enhanced in deuterium. The disclosed methods can be used to treat a skin disorder or an autoimmune disorder.

20 Claims, No Drawings

SHORT CHAIN FATTY ACID COMPOUNDS AND USES THEREOF

CROSS-REFERENCE TO RELATED APPLICATIONS

This application is a Continuation of International Patent Application No. PCT/US2024/061643, filed on Dec. 23, 2024, which claims priority to and the benefit of U.S. Provisional Application No. 63/614,077, filed on Dec. 22, 2023, each of which are incorporated herein by reference in their entirety.

BACKGROUND

Short chain fatty acids (SCFAs) are saturated aliphatic acids consisting of one polar carboxylic acid moiety and hydrophobic hydrocarbon chain. Among these, acetate (C2), propionate (C3) and butyrate (C4) are the most common and well-studied molecules.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Disclosed herein is a pharmaceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) a solid pharmaceutically-acceptable excipient.

Disclosed herein is a pharmaceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and (b) a solid pharmaceutically-acceptable excipient.

Disclosed herein is a pharmaceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein: $H^{a1}$ is a population of isotopes of hydrogen that is about a natural abundance of isotopes of hydrogen or a population of isotopes of hydrogen that is at least 1% deuterium; $H^{b1}$ is a population of isotopes of hydrogen that is about a natural abundance of isotopes of hydrogen or a population of isotopes of hydrogen that is at least 1% deuterium; $H^{c1}$ is a population of isotopes of hydrogen that is about a natural abundance of isotopes of hydrogen or a population of isotopes of hydrogen that is at least 1% deuterium; $H^{d1}$ is a population of isotopes of hydrogen that is about a natural abundance of isotopes of hydrogen or a population of isotopes of hydrogen that is at least 1% deuterium; $H^{e1}$ is a population of isotopes of hydrogen that is about a natural abundance of isotopes of hydrogen or a population of isotopes of hydrogen that is at least 1% deuterium; $H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) a solid pharmaceutically-acceptable excipient.

Disclosed herein is a pharmaceutical composition comprising: (a) an amount of at least 1 mg of propionic acid or a pharmaceutically-acceptable salt thereof, wherein at least 1% of hydrogen atoms in the propionic acid or the pharmaceutically-acceptable salt thereof are deuterium; and (b) a solid pharmaceutically-acceptable excipient.

Disclosed herein is a pharmaceutical composition comprising: (a) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry; and (b) a solid pharmaceutically-acceptable excipient.

Disclosed herein is a pharmaceutical composition comprising: (a) an amount of at least 1 mg of: $(C(H^{a2})(H^{b2})(H^{c2}))$—$(C(H^{d2})(H^{e2}))$—COOH or a pharmaceutically-acceptable salt thereof, wherein: $H^{a2}$ is a population of isotopes of hydrogen that is about a natural abundance of isotopes of hydrogen or a population of isotopes of hydrogen that is at least 5% deuterium; $H^{b2}$ is a population of isotopes of hydrogen that is about a natural abundance of isotopes of hydrogen or a population of isotopes of hydrogen that is at least 5% deuterium; $H^{e2}$ is a population of isotopes of hydrogen that is about a natural abundance of isotopes of hydrogen or a population of isotopes of hydrogen that is at least 5% deuterium; $H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium; and (b) a solid pharmaceutically-acceptable excipient.

Disclosed herein is a pharmaceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) an amount of at least 1 mg of propionic acid or a pharmaceutically-acceptable salt thereof, wherein at least 1% of hydrogen atoms in the propionic acid or the pharmaceutically-acceptable salt thereof are deuterium.

Disclosed herein is a pharmaceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and b) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry.

Disclosed herein is a pharmaceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein: $H^{a1}$ is a population of isotopes of hydrogen that is about a natural abundance of isotopes of hydrogen or a population of isotopes of hydrogen that is at least 1% deuterium; $H^{b1}$ is a population of isotopes of hydrogen that is about a natural abundance of isotopes of hydrogen or a population of isotopes of hydrogen that is at least 1% deuterium; $H^{c1}$ is a population of isotopes of hydrogen that is about a natural abundance of isotopes of hydrogen or a population of isotopes of hydrogen that is at least 1% deuterium; $H^{d1}$ is a population of isotopes of hydrogen that is about a natural abundance of isotopes of hydrogen or a population of isotopes of hydrogen that is at least 1% deuterium; $H^{e1}$ is a population of isotopes of hydrogen that is about a natural abundance of isotopes of hydrogen or a population of isotopes of hydrogen that is at least 1% deuterium; $H^{f1}$ is a population of isotopes of hydrogen that is about a natural abundance of isotopes of hydrogen or a population of isotopes of hydrogen that is at least 1% deuterium; and $H^{e1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) an amount of at least 1 mg of: $(C(H^{a2})(H^{b2})(H^{c2}))$—$(C(H^{d2})(H^{e2}))$—COOH or a pharmaceutically-acceptable salt thereof, wherein: $H^{a2}$ is a population of isotopes of hydrogen that is about a natural abundance of isotopes of hydrogen or a population of isotopes of hydrogen that is at least 5% deuterium; $H^{b2}$ is a population of isotopes of hydrogen that is about a natural abundance of isotopes of hydrogen or a population of isotopes of hydrogen that is at least 5% deuterium; $H^{c2}$ is a population of isotopes of hydrogen that is about a natural abundance of isotopes of hydrogen or a population of isotopes of hydrogen that is at least 5% deuterium; $H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium.

DETAILED DESCRIPTION

Short Chain Fatty Acid (SCFA)

Short chain fatty acids (SCFAs) are fatty acids with aliphatic tails shorter than aliphatic tails of long chain fatty acids. Short chain fatty acids can be derivatized to provide a salt or ester thereof, for example, pharmaceutically-acceptable salts and esters of fatty acids (e.g., sodium butyrate, arginine butyrate).

In some embodiments, a composition disclosed herein comprises at least one SCFA. In some embodiments, a composition disclosed herein comprises at least one short chain fatty acid (SCFA), SCFA precursor, SCFA biosynthesis precursor, a derivative thereof, a SCFA moiety, or a combination thereof.

In some embodiments, a composition disclosed herein comprises at least one SCFA, or a compound comprising a SCFA moiety. In some embodiments, a composition disclosed herein comprises at least two SCFAs. In some embodiments, a composition disclosed herein comprises at least three SCFAs.

Non-limiting examples of a SCFA or SCFA moiety include: acetic acid, butyric acid (BA), C3-C12 fatty acids, C3-C10 fatty acids, C3-C8 fatty acids, methoxyacetic acid, valproic acid (VPA), propionic acid, 3-methoxypropionic acid, ethoxyacetic acid, formic acid, isobutyric acid, tributyrin, N-acetylbutyrate (and other forms of butyrate, e.g., phenylbutyrate, isobutyrate, pivaloyloxymethyl butyrate, monoacetone glucose 3-butyrate), isovaleric acid, valeric acid, isocaproic acid, caproic acid, lactic acid, succinic acid, pyruvic acid, octanoic acid, dodecanoic acid, (4R)-4-hydroxypentanoic acid, 2-ethylhydracrylic acid, 2-hydroxy-3-methylpentanoate, 2-hydroxy-3-methylpentanoic acid, 2-methylbut-2-enoic acid, 2-oxobutanoic acid, 3-hydroxypentanoic acid, 3-methylbut-2-enoic acid, butenoic acid, methylbutyric acid, dimethylbutyric acid, pentadienoic acid, pentenoic acid, pivalic acid, propynoic acid, and a combination thereof.

Non-limiting examples of a SCFA or a SCFA moiety include: compounds or structures with at least 12 carbon atoms, at least 11 carbon atoms, at least 10 carbon atoms, at least 9 carbon atoms, at least 8 carbon atoms, at least 7 carbon atoms, at least 6 carbon atoms, at least 5 carbon atoms, at least 4 carbon atoms, at least 3 carbon atoms, and at least 2 carbon atoms. In some embodiments, the SCFA or SCFA moiety includes compounds or structures with no greater than 13 carbon atoms, no greater than 12 carbon atoms, no greater than 11 carbon atoms, no greater than 10 carbon atoms, no greater than 9 carbon atoms, no greater than 8 carbon atoms, or no greater than 7 carbon atoms.

In some embodiments, a SCFA or SCFA moiety is not a branched fatty acid. In some embodiments, a SCFA or SCFA moiety is a branched fatty acid.

In some embodiments, short chain fatty acids (SCFAs) modulate a cytokine. In some embodiments, the cytokine is a pro-inflammatory cytokine. Non-limiting examples of cytokines include: TNFα, IFNγ, IL-17A, IL-21, IL-22, IL-23, IL-27, IL-31, and MIP-3α.

In some embodiments, short chain fatty acids (SCFAs) modulate multiple cellular signaling proteins, including, but not limited to, IL-18, TLR3, IFN-γ, TNFα, TGF-β, MyD88, PI3K/Akt, JAK/STAT, Smad 2/3, Smad 4, IL-10, Notch, hedgehog, Wnt (beta-catenin), matrix metalloproteinases 9 and 10, tissue inhibitor of metalloproteinases, nodal and NF-κB signaling. In some embodiments, the signaling proteins that are modulated by SCFAs modulate biological pathways or processes include, but are not limited to, inflammation, immunity, proliferation, differentiation, apoptosis, oncogenesis, transcription of DNA, cytokine production, cell survival, angiogenesis, fibrogenesis and cellular responses to stimuli such as stress, cytokines, free radicals, heavy metals, and ultraviolet irradiation.

In some embodiments, a method disclosed herein comprises treating or reducing a likelihood of developing medical diseases or disorders characterized by elevated levels or abnormal expression of at least one of IL-18, TLR3, IFN-γ, TNFα, TGF-β, MyD88, PI3K/Akt, JAK/STAT, Smad 2/3, Smad 4 or IL-10 signaling. In some embodiments, a method disclosed herein comprises treating or reducing a likelihood of developing medical diseases or disorders characterized by decreased levels or abnormal expression of NF-κB signaling.

In some embodiments, a composition disclosed herein comprises at least one compound comprising a precursor of a SCFA, or a moiety thereof. Non-limiting examples of the precursor include plant cell-wall polysaccharides, dietary nonstarch polysaccharides (NSP) a salt of lactate, a salt of succinate, a salt of formate, 1,2-propenedol, trypamine, indole, indole-3-acetate, and a combination thereof.

In some embodiments, a composition disclosed herein comprises at least one compound comprising a biosynthesis precursor of a SCFA, or a moiety thereof. Non-limiting examples of a biosynthesis precursor include acetyl-CoA carboxylase inhibitor, an adenosine monophosphate kinase (AMPK) activator, vitamin D, and a combination thereof.

In some embodiments, a composition disclosed herein comprises a salt of a SCFA, or a derivative thereof. Non-limiting examples of a salt of butyric acid include sodium butyrate, magnesium butyrate, and calcium butyrate. In some embodiments, the composition comprises one or more of magnesium butyrate and calcium butyrate.

In some embodiments, a composition disclosed herein comprises butyric acid or a pharmaceutically-acceptable salt thereof. In some embodiments, a composition disclosed herein comprises propionic acid or a pharmaceutically-acceptable salt thereof. In some embodiments, a composition disclosed herein comprises butyric acid or a pharmaceutically-acceptable salt thereof and propionic acid or a pharmaceutically-acceptable salt thereof.

Butyric acid is metabolized through the process of beta-oxidation. The steps involved in fatty acid metabolism include the following. (1) Fatty acids enter cells. (2) The fatty-acid-CoA ligase enzyme catalyzes the reaction between the fatty acid and ATP and CoA to yield a fatty acyl-CoA intermediate in a two-step process that goes through a fatty-acid-AMP intermediate. For example, Fatty acid+CoA+ATP=Acyl$\rightleftharpoons$ CoA+AMP+PPi. (3) Transport of the fatty-acid-CoA into the mitochondria of cells through the carnitine system. (4) The fatty-acid-CoA is transported into the mitochondria of cells through the carnitine system. The fatty acyl-CoA reacts with the acyl-CoA dehydrogenase enzyme to catalyze beta-oxidation in the mitochondria of cells. This step is slowed down by deuteration of butyric acid.

In some embodiments, a composition disclosed herein comprises acetic acid or a pharmaceutically-acceptable salt thereof. In some embodiments, a composition disclosed herein comprises butyric acid or a pharmaceutically-acceptable salt thereof, propionic acid or a pharmaceutically-acceptable salt thereof, and acetic acid or a pharmaceutically-acceptable salt thereof.

In some embodiments, a composition disclosed herein comprises a derivative of a SCFA. In some embodiments, the derivative comprises at least one SCFA moiety linked to at least one additional moiety. In some embodiments, the derivative comprises at least one SCFA moiety linked to at least one polyethylene glycol (PEG) moiety. In some embodiments, the SCFA moiety linked to the PEG moiety hydrolyzes under a low pH condition to yield a SCFA molecule and a PEG molecule.

In some embodiments, a composition disclosed herein a combination of SCFAs, and/or derivatives thereof. In some embodiments, the composition is prepared at amounts of at least 10 mM, at least 20 mM, at least 30 mM, at least 40 mM, at least 50 mM, at least 60 mM, at least 70 mM, at least 80 mM, at least 90 mM, at least 100 mM, or more of each or all the compounds of the composition.

Derivatives of SCFAs, e.g., having substituents on the carbon chain such as OH, SH, $NH_2$, methyl, ethyl, halogen, and other groups that do not interfere with the compound's therapeutic activity can also be used. In some embodiments, a compound disclosed herein comprises at least one SCFA linked to at least one additional moiety, such as OH, SH, $NH_2$, methyl, ethyl, halogen, and other groups that do not interfere with the compound's therapeutic activity. In some embodiments, a SCFA is pegylated.

In some embodiments, a composition disclosed herein comprises a precursor of a SCFA alone or in combination with one or more SCFAs. Non-limiting examples of precursors of SCFAs include: a salt of formate, a salt of lactate, a salt of succinate, 1,2-propenedol, trypamine, indole, and indole-3-acetate.

In some embodiments, a composition disclosed herein comprises a precursor of SCFA biosynthesis alone or in combination with one or more SCFA. Non-limiting examples of precursors of SCFA biosynthesis include: a salt of formate, a salt of lactate, a salt of succinate, acetyl-CoA carboxylase inhibitors, adenosine monophosphate kinase (AMPK) activators, and vitamin D.

In some embodiments, a compound comprising at least one SCFA, or a compound comprising a SCFA moiety disclosed herein is combined with one or more compounds, such as one or more additional therapeutic agent, for a particular disease or disorder. In some embodiments, the SCFA is in the same composition as one or more additional therapeutic agents. In some embodiments, the composition comprises at least 1, at least 2, at least 3, at least 4, at least 5, at least 6, at least 7, at least 8, at least 9, at least 10, or more than 10 additional therapeutic agents.

Compositions of the Disclosure

In some embodiments, compositions comprise one or more isotopically enriched atoms. For example, a hydrogen atom at a given position in a molecule can be isotopically enriched in deuterium (or deuterio group) above the natural abundance of deuterium in elemental hydrogen, resulting in the position being isotopically depleted in protium isotope. In some embodiments, one or more hydrogen atoms of a composition disclosed here in is isotopically enriched with a corresponding number of deuterium atoms. In some embodiments, all the hydrogen atoms in a compound are isotopically enriched in deuterium. In some embodiments, all the carbon-bound hydrogen atoms in a compound are isotopically enriched in deuterium. In some embodiments, all the non-acidic hydrogen atoms in a compound are isotopically enriched in deuterium.

In some embodiments, isotopic enrichment in deuterium can improve the metabolic stability and/or efficacy of a pharmaceutical compound, thus increasing the duration of action of drugs. In some embodiments, isotopic enrichment in deuterium can improve the metabolic stability and/or efficacy relative to a comparator, thus increasing the duration of action of drugs. For example, isotopic enrichment in deuterium can extend a molecule's biological half-life, for example, by increasing a molecule's resistance to metabolic degradation.

In some embodiments, resistance to biological degradation is at least partially related to the relative strength of the deuterium-carbon covalent bond in comparison to the protium-carbon covalent bond. The deuterium nucleus contains a proton and a neutron. The protium nucleus contains only a proton. Thus, the deuterium is about twice the mass of the protium nucleus. The greater mass of the deuterium nucleus results in the deuterium-carbon bond having a lower vibrational frequency than does a corresponding protium-carbon bond. This lower vibrational frequency results in a covalent bond that is shorter, and thus stronger. The higher strength provides resistance against metabolic degradation, such as hydrogen atom abstraction by cytochrome P450.

In some embodiments, the longer biological half-life of the compound isotopically-enriched in deuterium is thera-peutically-effective at a dosage that is lesser than the dosage of a corresponding compound that is not isotopically enriched in deuterium. The longer biological half-life results in slower elimination of the compound from the host. The longer residency time of the compounds results in a longer opportunity for the compound to exert a therapeutic effect. In some embodiments, this scenario results in a lesser quantity of the compound having efficacy in comparison to an analogous compound that is not isotopically enriched in deuterium. In some embodiments, this effect permits a dose reduction, which can be favorable.

In some embodiments, reduction of the amount of com-pound required for therapeutic effect can result in an improved therapeutic window for the compound. The thera-peutic window measures the dosage range from the mini-mum effective dose to the maximum tolerated dose. A wider therapeutic window suggests a favorable safety profile for a drug. A reduction in the minimum effective dose can result in an expanded therapeutic window.

In some embodiments, isotopically enriching a SCFA in deuterium comprises isotopically enriching a hydrogen atom of the SCFA with deuterium. In some embodiments, isoto-pically enriching a SCFA in deuterium improves the meta-bolic stability and/or efficacy of the SCFA. In some embodi-ments, isotopically enriching a SCFA in deuterium increases the biological half-life of the SCFA. In some embodiments, isotopically enriching a SCFA in deuterium increases the therapeutic window for the SCFA.

In some embodiments, the total isotopic enrichment of a sample of a compound herein can be measured. The total isotopic enrichment of all hydrogen atoms in a sample with deuterium can be, for example, at least 3,000 times greater than the natural abundance of deuterium; at least 3,500 times greater than the natural abundance of deuterium, at least 4,000 times greater than the natural abundance of deuterium, at least 4,500 times greater than the natural abundance of deuterium, at least 5,000 greater than the natural abundance of deuterium, at least 5,500 times greater than the natural abundance of deuterium, at least 6,000 times greater than the natural abundance of deuterium, or at least 6,500 times greater than the natural abundance of deuterium. The total isotopic enrichment of all hydrogen atoms in a sample with deuterium can be, for example, at least about 10 mol %, at least about 25 mol %, at least about 50 mol %, at least about 75 mol %, at least about 80 mol %, at least about 82.5 mol %, at least about 85 mol %, at least about 87.5 mol %, at least about 90 mol %, at least about 92.5 mol %, at least about 95 mol %, at least about 96 mol %, at least about 97 mol %, at least about 98 mol %, at least about 99 mol %, or at least about 99.5 mol %.

In some embodiments, the disclosure provides a pharma-ceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) a solid pharmaceutically-acceptable excipient.

In some embodiments, the disclosure provides pharma-ceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and (b) a solid pharmaceutically-acceptable excipient.

In some embodiments, the disclosure provides pharma-ceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein: $H^{a1}$ is a population of isotopes of hydrogen that is about a natural abundance of isotopes of hydrogen or a population of isotopes of hydrogen that is at least 1% deuterium; $H^{b1}$ is a population of isotopes of hydrogen that is about a natural abundance of isotopes of hydrogen or a population of isotopes of hydrogen that is at least 1% deuterium; $H^{c1}$ is a population of isotopes of hydrogen that is about a natural abundance of isotopes of hydrogen or a population of isotopes of hydrogen that is at least 1% deuterium; $H^{d1}$ is a population of isotopes of hydrogen that is about a natural abundance of isotopes of hydrogen or a population of isotopes of hydrogen that is at least 1% deuterium; $H^{e1}$ is a population of isotopes of hydrogen that is about a natural abundance of isotopes of hydrogen or a population of isotopes of hydrogen that is at least 1% deuterium; $H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) a solid pharmaceutically-acceptable excipient.

In some embodiments, the disclosure provides pharma-ceutical composition comprising: (a) an amount of at least 1 mg of propionic acid or a pharmaceutically-acceptable salt thereof, wherein at least 1% of hydrogen atoms in the propionic acid or the pharmaceutically-acceptable salt thereof are deuterium; and (b) a solid pharmaceutically-acceptable excipient.

In some embodiments, the disclosure provides pharma-ceutical composition comprising: (a) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry; and (b) a solid pharma-ceutically-acceptable excipient.

In some embodiments, the disclosure provides pharma-ceutical composition comprising: (a) an amount of at least 1 mg of: $(C(H^{a2})(H^{b2})(H^{c2}))$—$(C(H^{d2})(H^{e2}))$—COOH or a pharmaceutically-acceptable salt thereof, wherein: $H^{a2}$ is a population of isotopes of hydrogen that is about a natural abundance of isotopes of hydrogen or a population of isotopes of hydrogen that is at least 5% deuterium; $H^{b2}$ is a population of isotopes of hydrogen that is about a natural abundance of isotopes of hydrogen or a population of isotopes of hydrogen that is at least 5% deuterium; $H^{c2}$ is a population of isotopes of hydrogen that is about a natural abundance of isotopes of hydrogen or a population of isotopes of hydrogen that is at least 5% deuterium; $H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium; and (b) a solid pharmaceutically-acceptable excipient.

In some embodiments, the disclosure provides pharmaceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) an amount of at least 1 mg of propionic acid or a pharmaceutically-acceptable salt thereof, wherein at least 1% of hydrogen atoms in the propionic acid or the pharmaceutically-acceptable salt thereof are deuterium.

In some embodiments, the disclosure provides pharmaceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and b) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry.

In some embodiments, the disclosure provides pharmaceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein: $H^{a1}$ is a population of isotopes of hydrogen that is about a natural abundance of isotopes of hydrogen or a population of isotopes of hydrogen that is at least 1% deuterium; $H^{b1}$ is a population of isotopes of hydrogen that is about a natural abundance of isotopes of hydrogen or a population of isotopes of hydrogen that is at least 1% deuterium; $H^{c1}$ is a population of isotopes of hydrogen that is about a natural abundance of isotopes of hydrogen or a population of isotopes of hydrogen that is at least 1% deuterium; $H^{d1}$ is a population of isotopes of hydrogen that is about a natural abundance of isotopes of hydrogen or a population of isotopes of hydrogen that is at least 1% deuterium; $H^{e1}$ is a population of isotopes of hydrogen that is about a natural abundance of isotopes of hydrogen or a population of isotopes of hydrogen that is at least 1% deuterium; $H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) an amount of at least 1 mg of: $(C(H^{a2})(H^{b2})(H^{c2}))$—$(C(H^{d2})(H^{e2}))$—COOH or a pharmaceutically-acceptable salt thereof, wherein: $H^{a2}$ is a population of isotopes of hydrogen that is about a natural abundance of isotopes of hydrogen or a population of isotopes of hydrogen that is at least 5% deuterium; $H^{b2}$ is a population of isotopes of hydrogen that is about a natural abundance of isotopes of hydrogen or a population of isotopes of hydrogen that is at least 5% deuterium; $H^{c2}$ is a population of isotopes of hydrogen that is about a natural abundance of isotopes of hydrogen or a population of isotopes of hydrogen that is at least 5% deuterium; $H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium.

Psoriasis

Psoriasis is a chronic autoimmune disorder affecting the skin. The clinical appearance of psoriasis results from a dysregulated interaction between immune cells (e.g. dendritic cells [DCs] and T cells) and keratinocytes leading to inflammatory processes which drive the disease. The skin inflammation causes a rapid keratinocyte proliferation ending up in scaling of skin's surface, which shows a common phenotype of dry, raised, red skin lesions (plaques) covered with silvery scales.

Nonlimiting examples of psoriasis include: plaque psoriasis, guttate psoriasis, inverse psoriasis, pustular psoriasis, psoriasis vulgaris, seborrheic psoriasis erythrodermic psoriasis, nail psoriasis, and psoriatic arthritis.

In some embodiments, recruitment of innate and adaptive immune cells, which secrete pro-inflammatory cytokines, contribute to the pathogenesis of psoriasis. Cytokines play a critical role in the onset and progression of disease. Non-limiting examples of cytokines that contribute to the pathogenesis of psoriasis include IL-23 and IL-17.

Furthermore, Tregs are impaired in suppressive function leading to an altered T-helper 17/Treg balance. In some embodiments, cytokine antagonists (e.g. anti-TNFs like for instance Etanercept) are used in the treatment of plaque psoriasis (Ps) and psoriatic arthritis (PsA).

The IL-23/IL-17 immune axis can drive skin inflammation in psoriasis, which results from the interplay between keratinocytes and immune cells, such as Th17 cells. In some embodiments, pharmacological blockade of the IL-23/IL-17 immune axis results in clinical efficacy in psoriasis. In some embodiments, pharmacological modulation of the IL-23/IL-17 immune axis is evaluated by different drug modalities and administration (e.g., topical and systemic).

Human Th17 differentiation requires IL-1β, IL-6 and TGF-β and IL-23 to sustain production of IL-17 and IL-22 from Th17 cells. IL-17 induces expression of other pro-inflammatory mediators in keratinocytes, such as IL-17C, IL-19 and IL-36 that, together with IL-17 and IL-22, contribute to keratinocyte activation and epidermal hyperplasia, associated with expression of Keratin-16 and S100A7. In addition, increased levels of IFN-γ in psoriatic skin by activation of skin-resident Th1 cells contribute to the inflammatory activation of keratinocytes.

An autoimmune disease or disorder can include an immune response against a self-antigen that results in inflammation or destruction of healthy tissue in a subject, for example, a mammal, such as a human. Non-limiting examples of autoimmune diseases include arthritis (e.g., rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, psoriasis vulgaris, inverse psoriasis, erythrodermic psoriasis, seborrheic psoriasis and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis, respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopeniaurpura (TTP) and autoimmune or immune-mediated thrombocytopenia such as idiopathic thrombocytopeniaurpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, fibrosis of any organ or tissue, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In some embodiments, a method disclosed herein comprises treating a condition. In some embodiments the condition is a skin disorder. In some embodiments, the condition is psoriasis. In some embodiments, treating comprises causing disappearance of a psoriatic lesion in the subject in need thereof.

In some embodiments, a method disclosed herein comprising a SCFA disclosed herein reduces epidermal/dermal separation. In some embodiments, a method disclosed herein comprising a SCFA disclosed herein reduces a likelihood of degradation of the skin after inflammation.

Psoriasis Models

Preclinical skin models mimic the inflammatory features of psoriasis.

InflammaSkin® Psoriasis Model

The InflammaSkin® human psoriasis model is an ex vivo psoriasis skin model with a T-cell driven inflammation featuring the Th1/Th17 phenotype. This model allows for evaluation of the response of real human skin. Non-limiting examples of evaluation using an ex vivo psoriasis skin model include: evaluating response to prophylactic biologics, therapeutic biologics, and small molecule drugs after topical or subcutaneous administration.

Mouse imiquimod (IMQ)-induced psoriasis model induced psoriasis is a model representing most features of human psoriasis including phenotypical and histological characteristics of skin lesions and involvement of IL-23/IL-17 axis.

The mouse imiquimod (IMQ) psoriasis model is induced, for example, by the topical administration of Aldara cream (containing 5% of the TLR7/8 ligand IMQ; Meda Pharma GmbH) to the shaved back skin and the ear of female Balb/c (approx. 20 g) mice, is used to evaluate pathogenic mechanisms involved in psoriasis development, and to analyze possible new therapies for psoriasis.

Mouse Imiquimod (IMQ) Model

Daily repeated applications of IMQ over 6 consecutive days rapidly induces skin inflammation in mice with pathologic and histologic features to human psoriasis, including the development of skin erythema and scaling, epidermal thickening (acanthosis), altered keratinocyte differentiation, neoangiogenesis, and skin infiltration of immune cells. The involvement of a dysregulated IL-23/IL-17 axis and the overproduction of other inflammatory cytokines, like IL-1, IL-36, and IL-22, which are pathways involved in human psoriasis, are mirrored in the IMQ-induced psoriasis.

Conditions

The present disclosure describes methods and systems for treating conditions comprising administering a pharmaceutical composition comprising at least one short chain fatty acid (SCFA), a SCFA precursor, a SCFA biosynthesis precursor, a compound comprising a SFCA moiety, a derivative thereof, and a combination thereof, wherein the SCFA is at least partially isotopically enhanced in deuterium. In some embodiments, the condition is a skin disorder. In some embodiments, the condition is psoriasis. In some embodiments, the condition is an autoimmune disorder.

Disclosed herein is a method for the treatment or reducing a likelihood of developing at least one disease or disorder in a subject, comprising administering to the subject at least one composition comprising a SCFA or a compound comprising a SCFA moiety, wherein the SCFA is at least partially isotopically enhanced in deuterium, optionally in combination with at least one additional agent or therapy.

In some embodiments, a composition disclosed herein increases the number of disease-free days, reduce the severity of a disease or disorder, reduce the risk of developing a disease or disorder, reduce the risk of recurrence of a disease or disorder, or a combination thereof in the subject. In some embodiments, a composition disclosed herein increase the number of disease-free days by at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60% or more in the subject as compared to a subject who is not receiving treatment. In some embodiments, a composition disclosed herein reduce the severity of a disease or disorder by at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60% or more in the subject as compared to a subject who is not receiving treatment. In some embodiments, a composition disclosed herein reduce the risk of developing a disease or disorder by at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60% or more in the subject as compared to a subject who is not receiving treatment. In some embodiments, a composition disclosed herein reduce the risk of recurrence of a disease or disorder by at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60% or more in the subject as compared to a subject who is not receiving treatment.

Non-limiting examples of diseases and disorders that are treated, reduced in likelihood, or ameliorated include: inflammatory diseases and various cancer diseases. Non-limiting examples of inflammatory diseases and disorders include: asthma, arthritis, allergic rhinitis, psoriasis, atopic dermatitis, inflammatory bowel diseases, Crohn's disease, an allergic or autoimmune disease or disorder associated with C-section delivery of a neonate, uveitis, and vasculitis.

Skin Disorders

In some embodiments, a SCFA disclosed herein is effective in the treatment of a skin disorder. In some embodiments, a combination of at least one SCFA with at least one other skin disorder treatment can be effective as a therapeutic approach for the treatment of a skin disorder.

Disclosed herein is a method for treatment, inhibition, prevention, or reduction of a skin disease or disorder by administering a composition comprising a SCFA, as disclosed herein, to a subject in need thereof, optionally in combination with at least one additional agent or therapy. Non-limiting examples of skin diseases and disorders include: psoriasis, plaque psoriasis, guttate psoriasis, inverse psoriasis, pustular psoriasis, psoriasis vulgaris, seborrheic psoriasis, erythrodermic psoriasis, nail psoriasis, psoriatic arthritis, systemic lupus erythematosus (SLE) rash, scleroderma (systemic sclerosis), diabetes related skin conditions, rheumatoid arthritis and associated skin rashes (rheumatoid vasculitis), melanoma, vitiligo, eczema (atopic dermatitis), dyshidrotic eczema, rosacea, hives, impetigo, cellulitis, contact dermatitis, canker sores, acne, Lichen planus, actinic keratosis, ichthyosis vulgaris, dermatomyositis, and pemphigoid.

Disclosed herein is a method for treatment, inhibition, prevention, or reduction of a skin disease or disorder, comprising administering a composition comprising a SCFA, as disclosed herein, to a subject in need thereof.

In some embodiments, a subject suffering from a skin disorder is a human. In some embodiments, a subject suffering from a skin disorder is a non-human animal.

In some embodiments, a composition disclosed herein comprises at least one SCFA and at least one second compound for use as a therapeutic for the treatment of skin disorders. In some embodiments, a SCFA comprises one or more of formic acid, acetic acid, propionic acid, isobutyric acid, butyric acid, tributyrin, N-acetylbutyrate (and other forms of butyrate), isovaleric acid, valeric acid, isocaproic acid, caproic acid, lactic acid, succinic acid, pyruvic acid, octanoic acid, and dodecanoic acid. In some embodiments, a second compound comprises one or more of a PDE4 inhibitor, an anti-inflammatory compound, a disease-modifying antirheumatic drug (DMARD), an immunosuppressant, a biologic agent, and a Cox-2 inhibitor.

In some embodiments, a composition for use in methods of treating skin disorders comprises an amount of a form of a butyrate salt that is isotopically enriched in deuterium, wherein the amount is therapeutically equivalent to about 1200 mg of a salt of butyrate ion that has a natural abundance of hydrogen nuclei, for example, a sodium, calcium, or magnesium salt, an amount of a form of a propionate salt that is isotopically enriched in deuterium, wherein the amount is therapeutically equivalent to about 39 mg of a salt of propionate ion that has a natural abundance of hydrogen nuclei, for example, a sodium, calcium, or magnesium salt, about 7 mg of a source of magnesium, for example, magnesium chloride or magnesium hydroxide, and about 0.1 mg of a vitamin D, for example, vitamin D3.

In some embodiments, a composition for use in methods of treating skin disorders comprises an amount of a form of a butyrate salt that is isotopically enriched in deuterium, wherein the amount is therapeutically equivalent to about 800 mg of a salt of butyrate ion that has a natural abundance of hydrogen nuclei, for example, a sodium, calcium, or magnesium salt, an amount of a form of a propionate salt that is isotopically enriched in deuterium, wherein the amount is therapeutically equivalent to about 50 mg of a salt of propionate ion that has a natural abundance of hydrogen nuclei, for example, a sodium, calcium, or magnesium salt, about 10 mg of a source of magnesium, for example, magnesium chloride or magnesium hydroxide, and about 40 IU of a vitamin D, for example, vitamin D3.

In some embodiments, a composition for use in methods of treating skin disorders comprises an amount of a form of a butyrate salt that is isotopically enriched in deuterium, wherein the amount is therapeutically equivalent to about 900 mg of a salt of butyrate ion that has a natural abundance of hydrogen nuclei, for example, a sodium, calcium, or magnesium salt, an amount of a form of a propionate salt that is isotopically enriched in deuterium, wherein the amount is therapeutically equivalent to about 100 mg of a salt of propionate ion that has a natural abundance of hydrogen nuclei, for example, a sodium, calcium, or magnesium salt, about 10 mg of a source of magnesium, for example, magnesium chloride or magnesium hydroxide, and about 50 IU of a vitamin D, for example, vitamin D3. In some embodiments, the composition further comprises about 10 mg apremilast. In some embodiments, the composition is co-administered with a unit dosage form of about 10 mg apremilast.

In some embodiments, an example of a daily oral dosage for use in methods of treating skin disorders comprises an amount of a form of butyric acid or a pharmaceutically-acceptable salt thereof that is isotopically enriched in deuterium, wherein the amount is therapeutically equivalent to about 3600 mg of butyric acid or a pharmaceutically-acceptable salt thereof that has a natural abundance of hydrogen nuclei, for example, a sodium, calcium, or magnesium salt, an amount of a form of a propionate acid or a pharmaceutically-acceptable salt thereof that is isotopically enriched in deuterium, wherein the amount is therapeutically equivalent to about 400 mg of a salt of propionate ion that has a natural abundance of hydrogen nuclei, for example, a sodium, calcium, or magnesium salt, about 40 mg of a source of magnesium, for example, magnesium chloride or magnesium hydroxide, and about 200 IU of a vitamin D, for example, vitamin D3.

In some embodiments, an example of a dosage for use in methods of treating skin disorders comprises a form of butyric acid or a pharmaceutically-acceptable salt thereof that is isotopically enriched in deuterium, wherein the amount is therapeutically equivalent to about 700 mg to about 1,800 mg of butyric acid or a pharmaceutically-acceptable salt thereof that has a natural abundance of hydrogen nuclei, for example, a sodium, calcium, or magnesium salt, an amount of a form of a propionate acid or a pharmaceutically-acceptable salt thereof that is isotopically enriched in deuterium, wherein the amount is therapeutically equivalent to about 200 mg to about 300 mg of a salt of propionate ion that has a natural abundance of hydrogen nuclei, for example, a sodium, calcium, or magnesium salt, about 5 mg to about 20 mg of a source of magnesium, for example, magnesium chloride or magnesium hydroxide, and about 200 IU of a vitamin D, for example, Vitamin D3 administered 1-4 times daily.

In some embodiments, a composition is administered 1-4 times daily for at least 1 week, at least 2 weeks, at least 3 weeks or for more than 3 weeks.

In some embodiments, an example dosage for use in methods of treating skin disorders comprises an amount of a form of butyric acid or a pharmaceutically-acceptable salt thereof that is isotopically enriched in deuterium, wherein the amount is therapeutically equivalent to about 1 to about 2 g of butyric acid or a pharmaceutically-acceptable salt thereof that has a natural abundance of hydrogen nuclei, for example, a sodium, calcium, or magnesium salt, an amount of a form of a propionate acid or a pharmaceutically-acceptable salt thereof that is isotopically enriched in deuterium, wherein the amount is therapeutically equivalent to about 100 mg of propionic acid or a pharmaceutically-acceptable salt thereof that has a natural abundance of hydrogen nuclei, for example, a sodium, calcium, or magnesium salt, about 10 mg to about 15 mg Otezla, about 10 mg to about 20 mg of a source of magnesium, for example, magnesium chloride or magnesium hydroxide, and about 80 to about100 IU of a vitamin D, for example, Vitamin D3.

In some embodiments, a composition comprising at least one SCFA is an enteric coated, extended release, and sustained release capsule.

In some embodiments, a method of treating skin disorders comprises administration of an oral formulation of a SCFA in combination with a topical ointment. An example of a topical ointment for use in treating skin disorder comprises about 40% clobetazol (0.05%) cream, about 20% calcipotriene (vit D, 0.005%) cream, about 20% vit E (0.5%) cream, and about 20% salicylic acid (10%) cream. Another example of a topical ointment for use in treating skin disorder comprises about 40% clobetazol (0.05%) cream, about 20% calcipotriene (vit D, 0.005%) cream, about 20% vit E (0.5%) cream, and about 20% zinc cream. In some embodiments, zinc is used together with salicylic acid in a topical ointment.

Dosing and Administration

In practicing the methods or use provided herein, therapeutically-effective amounts of the compounds described herein are administered to a subject having a disease or condition to be treated. A therapeutically-effective amount can vary widely depending on the severity of the disease, the age and relative health of the subject, the potency of the compounds used, and other factors. Subjects can be, for example, humans, elderly adults, adults, adolescents, pre-adolescents, children, toddlers, infants, or neonates. A subject can be a patient.

The particular dosage of a compound required to treat the condition can depend on the severity of the condition, the route of administration, and related factors that can be decided by the attending physician.

A therapeutically-effective amount of a compound of the present disclosure can be expressed as mg of the compound per kg of subject body mass. In some embodiments, a therapeutically-effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, a therapeutically-effective amount is about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

A compound described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 325 mg, from about 325 mg to about 350 mg, from about 350 mg to about 400 mg, from about 400 mg to about 425 mg, from about 425 mg to about 450 mg, from about 450 mg to about 500 mg, from about 500 mg to about 525 mg, from about 525 mg to about 550 mg, from about 550 mg to about 600 mg, from about 600 mg to about 625 mg, from about 625 mg to about 650 mg, from about 650 mg to about 700 mg, from about 700 mg to about 725 mg, from about 725 mg to about 750 mg, from about 750 mg to about 800 mg, from about 800 mg to about 825 mg, from about 825 mg to about 850 mg, from about 850 mg to about 900 mg, from about 900 mg to about 925 mg, from about 925 mg to about 950 mg, from about 950 mg to about 1000 mg, from about 1000 mg to about 1025 mg, from about 1025 mg to about 1050 mg, from about 1050 mg to about 1100 mg, from about 1100 mg to about 1125 mg, from about 1125 mg to about 1150 mg, from about 1150 mg to about 1200 mg, from about 1200 mg to about 1225 mg, from about 1225 mg to about 1250 mg, from about 1250 mg to about 1300 mg, from about 1300 mg to about 1325 mg, from about 1325 mg to about 1350 mg, from about 1350 mg to about 1400 mg, from about 1400 mg to about 1425 mg, from about 1425 mg to about 1450 mg, from about 1450 mg to about 1500 mg, from about 1500 mg to about 1525 mg, from about 1525 mg to about 1550 mg, from about 1550 mg to about 1600 mg, from about 1600 mg to about 1625 mg, from about 1650 mg to about 1700 mg, from about 1700 mg to about 1725 mg, from about 1725 mg to about 1750 mg, from about 1750 mg to about 1800 mg, from about 1800 mg to about 1825 mg, from about 1825 mg to about 1850 mg, from about 1850 mg to about 1900 mg, 1900 mg to about 1925 mg, from about 1925 mg to about 1950 mg, or from about 1950 mg to about 2000 mg.

A compound described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg about 1225 mg, about 1250 mg, about 1275 mg, about 1300 mg about 1325 mg, about 1350 mg, about 1375 mg, about 1400 mg about 1425 mg, about 1450 mg, about 1475 mg, about 1500 mg about 1525 mg, about 1550 mg, about 1575 mg, about 1600 mg about 1625 mg, about 1650 mg, about 1675 mg, about 1700 mg about 1725 mg, about 1750 mg, about 1775 mg, about 1800 mg about 1825 mg, about 1850 mg, about 1875 mg, about 1900 mg about 1925 mg, about 1950 mg, about 1975 mg, or about 2000 mg.

In some embodiments, a therapeutically-effective amount can be administered 1-35 times per week, 1-14 times per week, or 1-7 times per week. In some embodiments, a therapeutically-effective amount can be administered 1-10 times per day, 1-5 times per day, 1 time, 2 times, or 3 times per day.

In some embodiments, a number of doses for a therapeutically-effective amount can be 1, 2, 3, 4, 5, 6, 7, 8, 9, 10, or more than 10.

In some embodiments, a compound disclosed herein can be administered in therapeutically-effective amounts by various forms and routes including, for example, by intravenous, intravitreal, subcutaneous, intramuscular, oral, rectal, aerosol, parenteral, ophthalmic, pulmonary, transdermal, vaginal, otic, nasal, intraocular, and topical administration. Non-limiting examples of parenteral or systemic administration include subcutaneous, intravenous, intraperitoneal, and intramuscular injections.

In some embodiments, a pharmaceutical composition disclosed herein is generally formulated for oral or topical (i.e., skin, ocular and mucosal surfaces) administration, with the most suitable route in any given case depending on the nature and severity of the condition being treated and on the nature of the particular active agent which is being used.

Topical Formulations

In some embodiments, a pharmaceutical composition, composition, or compound disclosed herein, can be administered topically, and thus be formulated in a form suitable for topical administration, i.e. as a pH balanced cream preparation. An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin at a more consistent rate, than a formulation having a lesser concentration, all other things being equal.

Formulations suitable for topical administration include, but are not limited to, liquid or semi liquid preparations such as liniments, lotions, oil in water or water in oil emulsions such as creams, ointments or pastes, and solutions or suspensions. Further, formulations suitable for topical administration can be in the form of cremes and liquids including, for example, syrups, suspensions or emulsions, inhalants, sprays, mousses, oils, gels, and solids. Topically administrable formulations can, for example, comprise from about 1% to about 10% (w/w) active ingredient. Although the concentration of the active ingredient can be as high as the solubility limit of the active ingredient in the solvent. Formulations for topical administration can further comprise one or more of the additional ingredients described herein.

Enhancers of permeation may be used. These materials increase the rate of penetration of drugs across the skin. Non-limiting examples of enhancers include ethanol, glycerol monolaurate, PGML (polyethylene glycol monolaurate), and dimethylsulfoxide. Other enhancers include oleic acid, oleyl alcohol, ethoxydiglycol, laurocapram, alkanecarboxylic acids, dimethylsulfoxide, polar lipids, and N-methyl-2-pyrrolidone.

In some embodiments, the topically active pharmaceutical composition is combined with other ingredients such as adjuvants, anti-oxidants, chelating agents, surfactants, foaming agents, wetting agents, emulsifying agents, viscosifiers, buffering agents, or preservatives. In some embodiments, a permeation or penetration enhancer is included in the composition and is effective in improving the percutaneous penetration of the active ingredient into and through the stratum corneum with respect to a composition lacking the permeation enhancer. Non-limiting examples of permeation enhancers include oleic acid, oleyl alcohol, ethoxydiglycol, laurocapram, alkanecarboxylic acids, dimethylsulfoxide, polar lipids, or N-methyl-2-pyrrolidone. In some embodiments, the composition further comprises a hydrotropic agent, which functions to increase disorder in the structure of the stratum corneum, and thus allows increased transport across the stratum corneum. Non-limiting examples of hydrotropic agents include isopropyl alcohol, propylene glycol, and sodium xylene sulfonate.

The topically active pharmaceutical composition should be applied in an amount effective to effect desired changes. In some embodiments, an active compound is present in an amount of from about 0.0001% to about 15% by weight volume of the composition, from about 0.0005% to about 5% of the composition, or from about 0.001% to about 1% of the composition.

Oral Formulations

In some embodiments, a pharmaceutical composition, composition, or compound disclosed herein, is administered orally, and thus be formulated in a form suitable for oral administration, i.e. as a solid or a liquid preparation. Suitable solid oral formulations include tablets, capsules, pills, granules, and pellets. Suitable liquid oral formulations include solutions, suspensions, dispersions, emulsions, and oils. If formulated as a capsule, the compositions disclosed herein comprise, in addition to the active compound and the inert carrier or diluent, a hard gelating capsule. In some embodiments, a formulation for oral administration is an enteric coated, time release capsule.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy, which includes bringing into association the active compound and a suitable carrier (which can contain one or more accessory ingredients as noted above). In general, the formulations disclosed herein are prepared by uniformly and intimately admixing the active compound with a liquid or finely divided solid carrier, or both, and then, if necessary, shaping the resulting mixture. For example, a tablet can be prepared by compressing or molding a powder or granules containing the active compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

The delayed release dosage units can be coated with the delayed release polymer coating using conventional techniques, e.g., using a conventional coating pan, an airless spray technique, fluidized bed coating equipment (with or without a Wurster insert).

An example method for preparing extended release tablets is by compressing a drug-containing blend, e.g., blend of granules, prepared using a direct blend, wet-granulation, or dry-granulation process. Extended release tablets can also be molded rather than compressed, starting with a moist material containing a suitable water-soluble lubricant. However, tablets are manufactured using compression rather than molding. A method for forming extended release drug-containing blend is to mix drug particles directly with one or more excipients such as diluents (or fillers), binders, disintegrants, lubricants, glidants, and colorants. As an alternative to direct blending, a drug-containing blend can be prepared by using wet-granulation or dry-granulation processes. Beads containing the active agent can also be prepared by any one of a number of techniques, starting from a fluid dispersion. For example, a method for preparing drug-containing beads involves dispersing or dissolving the active agent in a coating suspension or solution containing pharmaceutical excipients such as polyvinylpyrrolidone, methylcellulose, talc, metallic stearates, silicone dioxide, or plasticizers. The admixture is used to coat a bead core such as a sugar sphere having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Delayed release formulations are created by coating a solid dosage form with a film of a polymer which is insoluble in the acid environment of the stomach, and soluble in the neutral environment of small intestines. The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Examples of coating materials include bioerodible, gradually hydrolyzable, gradually water-soluble, and/or enzymatically degradable polymers, and can be enteric polymers. Enteric polymers become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Non-limiting examples of coating materials for effecting delayed release include cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, e.g., formed from acrylic acid, methacrylic acid, methyl acrylate, ethyl acrylate, methyl methacrylate and/or ethyl methacrylate, and other methacrylic resins that are commercially available under the tradename Eudragit®, including Eudragit® L30D-55 and L100-55 (soluble at pH 5.5 and above), Eudragit®. L-100 (soluble at pH 6.0 and above), Eudragit®. S (soluble at pH 7.0 and above, as a result of a higher degree of esterification), and Eudragits®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum, zein, and shellac. Combinations of different coating materials can be used. Multi-layer coatings using different polymers can be applied.

The coating composition can include conventional additives, such as plasticizers, pigments, colorants, stabilizing agents, glidants, etc. A plasticizer reduces the fragility of the coating and can be represent about 10 wt. % to 50 wt. % relative to the dry weight of the polymer. Non-limiting examples of plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil, and acetylated monoglycerides. A stabilizing agent is used to stabilize particles in the dispersion. Typical stabilizing agents are nonionic emulsifiers such as sorbitan esters, polysorbates and polyvinylpyrrolidone. Glidants can reduce sticking effects during film formation and drying and can represent approximately 25 wt. % to 100 wt. % of the polymer weight in the coating solution. One glidant is talc. Other glidants such as magnesium stearate and glycerol monostearates can be used. Pigments such as titanium dioxide can be used. Small quantities of an anti-foaming agent, such as a silicone (e.g., simethicone), can be added to the coating composition.

In addition to a therapeutic or diagnostic agent (or possibly other desired molecules for delivery), the particles can include excipients such as a sugar, such as lactose, a protein, such as albumin, and/or a surfactant.

In some embodiments, a treatment regimen comprises daily oral administration of a short chain fatty acid. In some embodiments, an amount of a form of butyric acid or a pharmaceutically-acceptable salt thereof that is isotopically enriched in deuterium, wherein the amount is therapeutically equivalent to about 600 mg of butyric acid or a pharmaceutically-acceptable salt thereof, such as sodium butyrate, calcium butyrate, or magnesium butyrate, that has a natural abundance of hydrogen nuclei is administered 3 times per day (a total of about 1800 mg/day) for at least one week. In some embodiments, a treatment regimen comprises oral administration of two capsules, each containing an amount of a form of butyric acid or a pharmaceutically-acceptable salt thereof that is isotopically enriched in deuterium, wherein the amount is therapeutically equivalent to about 600 mg of butyric acid or a pharmaceutically-acceptable salt thereof, such as sodium butyrate, calcium butyrate, or magnesium butyrate, that has a natural abundance of hydrogen nuclei 3 times per day (a total of about 3,600 mg/day) for at least one week. In some embodiments, a treatment regimen comprises oral administration of two capsules, each containing an amount of a form of butyric acid or a pharmaceutically-acceptable salt thereof that is isotopically enriched in deuterium, wherein the amount is therapeutically equivalent to about 600 mg of butyric acid or a pharmaceutically-acceptable salt thereof, such as sodium butyrate, calcium butyrate, or magnesium butyrate, that has a natural abundance of hydrogen nuclei 3 times per day (a total of about 3,600 mg/day) for at least one week followed thereafter by oral administration of capsules, each containing an amount of a form of butyric acid or a pharmaceutically-acceptable salt thereof that is isotopically enriched in deuterium, wherein the amount is therapeutically equivalent to about 600 mg of butyric acid or a pharmaceutically-acceptable salt thereof, such as sodium butyrate calcium butyrate, or magnesium butyrate, that has a natural abundance of hydrogen nuclei 3 times per day (a total of about 1800 mg/day) for at least one week.

Compounds of the present disclosure, whether administered alone, or in combination with a modulator of oxidative stress can be administered to a subject in need of such administration, for example a human or animal patient.

Pharmaceutical Compositions

A pharmaceutical composition can be a combination of any compounds described herein with other chemical components, such as pharmaceutically acceptable carriers, stabilizers, binders, diluents, dispersing agents, suspending agents, thickening agents, solubilizing agents, or excipients. Such compositions can be in the form of, for example, granules, powders, tablets, capsules, syrup, suppositories, injections, emulsions, elixirs, suspensions, or solutions. The pharmaceutical composition facilitates administration of the compound to an organism.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N. Y., 1980; and Pharmaceutical Dosage Forms and Drug Delivery Systems, Seventh Ed. (Lippincott Williams & Wilkins 1999), each of which is incorporated by reference in its entirety.

In some embodiments, the pharmaceutical composition provided herein comprises a buffer as an excipient. Non-limiting examples of buffers include potassium phosphate, sodium phosphate, phosphate buffer, citrate buffer, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino) propanesulfonic acid buffer (MOPS), and piperazine-N,N'-bis(2-ethanesulfonic acid) buffer (PIPES), citric acid monohydrate, sodium dihydrogen phosphate, potassium dihydrogen phosphate, and any combination thereof.

In some embodiments, the pharmaceutical composition provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and any combination thereof.

Pharmaceutical preparations can be formulated with polyethylene glycol (PEG). PEGs with molecular weights ranging from about 300 g/mol to about 10,000,000 g/mol can be used. Non-limiting examples of PEGs include PEG 200, PEG 300, PEG 400, PEG 540, PEG 550, PEG 600, PEG 1000, PEG 1450, PEG 1500, PEG 2000, PEG 3000, PEG 3350, PEG 4000, PEG 4600, PEG 6000, PEG 8000, PEG 10,000, and PEG 20,000.

Further excipients that can be used in a composition described herein include, for example, benzalkonium chloride, benzethonium chloride, benzyl alcohol, butylated hydroxyanisole, butylated hydroxytoluene, chlorobutanol, dehydroacetic acid, ethylenediamine, ethyl vanillin, glycerin, hypophosphorous acid, phenol, phenylethyl alcohol, phenylmercuric nitrate, potassium benzoate, potassium metabisulfite, potassium sorbate, sodium bisulfite, sodium metabisulfite, sorbic acid, thimerasol, acetic acid, aluminum monostearate, boric acid, calcium hydroxide, calcium stearate, calcium sulfate, calcium tetrachloride, cellulose acetate pthalate, microcrystalline celluose, chloroform, citric acid, edetic acid, and ethylcellulose.

In some embodiments, the pharmaceutical composition provided herein comprises an aprotic solvent as an excipient. Non-limiting examples of aprotic solvents include perfluorohexane, α,α,α-trifluorotoluene, pentane, hexane, cyclohexane, methylcyclohexane, decalin, dioxane, carbon tetrachloride, freon-11, benzene, toluene, carbon disulfide, diisopropyl ether, diethyl ether, t-butyl methyl ether, ethyl acetate, 1,2-dimethoxyethane, 2-methoxyethyl ether, tetrahydrofuran, methylene chloride, pyridine, 2-butanone, acetone, N-methylpyrrolidinone, nitromethane, dimethylformamide, acetonitrile, sulfolane, dimethyl sulfoxide, and propylene carbonate.

The amount of the excipient in a pharmaceutical composition described herein can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of a compound in the pharmaceutical formulation.

The amount of the excipient in a pharmaceutical composition described herein can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form.

In some embodiments, the addition of an excipient to a pharmaceutical composition described herein can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical composition described herein can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%.

A composition disclosed herein can be used as a complete food product, as a component of a food product, as a dietary supplement, as part of a dietary supplement, or as a feed additive, and can be either in liquid, semisolid or solid form. A composition disclosed herein can be in the form of a pharmaceutical composition. The compositions, dietary supplements, food products, baby food products, feed additives, and/or pharmaceutical compositions disclosed herein can advantageously be utilized in methods for promoting the health of an individual.

A composition disclosed herein can be in liquid, semi-solid, or solid form. For example, the compositions can be administered as tablets, gel packs, capsules, gelatin capsules, flavored drinks, as a powder that can be reconstituted into such a drink, cooking oil, salad oil or dressing, sauce, syrup, mayonnaise, or margarine. Non-limiting examples of the food product and dietary supplements can include dairy products, baby food, baby formula, beverages, bars, a powder, a food topping, a drink, a cereal, an ice cream, a candy, a snack mix, a baked food product, and a fried food product. Non-limiting examples of beverages include energy drinks, nutraceutical drinks, smoothies, sports drinks, orange juice, and other fruit drinks. Non-limiting examples of a bar include a meal replacement, a nutritional bar, a snack bar, an energy bar, and an extruded bar. Non-limiting examples of a dairy product include yogurt, yogurt drinks, cheese, and milk.

In some embodiments, a food products or dietary supplements can further comprise herbals, herbal extracts, fungal extracts, enzymes, fiber sources, minerals, and vitamins. In some embodiments, a microalgal oils and microalgal biomass can be used in the compositions disclosed herein for both therapeutic and non-therapeutic uses. Thus, the compositions, food products, and animal feed additives disclosed herein can be used for therapeutic or non-therapeutic purposes.

In some embodiments, a method disclosed herein comprises treating a condition. In some embodiments the condition is a skin disorder. In some embodiments, the condition is psoriasis. In some embodiments, treating comprises causing disappearance of a psoriatic lesion in the subject in need thereof. In some embodiments, a method disclosed herein reduces epidermal/dermal separation. In some embodiments, a method disclosed herein reduces or prevents degradation of the skin after inflammation.

In some embodiments, a therapeutically-effective amount can be an amount effective in treating a condition, treating a skin disorder, treating psoriasis, or treating an autoimmune disorder. In some embodiments, a therapeutically-effective amount can be an amount effective in causing disappearance of a psoriatic lesion in the subject in need thereof. The disappearance of a psoriatic lesion can be by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 99%.

In some embodiments, a therapeutically-effective amount can be an amount effective in reduces epidermal/dermal separation in the skin. The epidermal/dermal separation can be reduced in size by at least about 10%, at least about 15%, at least about 0%, at least about 25%, at least about 30%, at least about 35%, at least about 40%, at least about 45%, at least about 50%, at least about 60%, at least about 70%, at least about 80%, at least about 90%, or at least about 99%.

In some embodiments, a therapeutically-effective amount can be an amount effective in prevents degradation of the skin after inflammation.

Pharmaceutically-Acceptable Salts

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, piprazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a piprazole salt, an imidazole salt, or a pyrazine salt.

Acid addition salts can arise from the addition of an acid to a compound described herein. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Combinations

In some embodiments, a method disclosed herein further comprises administering a therapeutically-effective amount of a second therapy. In some embodiments, the second therapy exhibits synergy with a short chain fatty acid, for example as provided herein, or a pharmaceutically-acceptable salt thereof. In some embodiments, the second therapy exhibits an additive therapeutic effect to the short chain fatty, for example as provided herein, acid or a pharmaceutically-acceptable salt thereof. In some embodiments, the short chain fatty acid, for example as provided herein, or a pharmaceutically-acceptable salt thereof exhibits an additive therapeutic effect to the second therapy.

In some embodiments, a method disclosed herein comprises administering to a subject in need thereof a therapeutically-effective amount of a short chain fatty acid, for example as provided herein, or a pharmaceutically-acceptable salt thereof and a reduced amount of a second therapy, wherein the reduced amount of the second therapy is therapeutically effective for treating the condition in combination with the therapeutically-effective amount of the short chain fatty acid, for example as provided herein, or a pharmaceutically-acceptable salt thereof, and wherein the reduced amount of the second therapy is less than an amount of the second therapy that is therapeutically effective for the condition in absence of the therapeutically-effective amount of the short chain fatty acid, for example as provided herein, or a pharmaceutically-acceptable salt thereof.

In some embodiments, a combination can be in a single formulation or can be separate and administered in sequence (either a composition comprising at least one SCFA, for example as provided herein, or a molecule comprising a SCFA moiety, first and then a composition comprising an additional agent, or a composition comprising an additional agent first and then a composition comprising at least one SCFA, for example as provided herein, or a molecule comprising a SCFA moiety). In some embodiments, the SCFA, for example as provided herein, or a molecule comprising a SCFA moiety, can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the composition comprising at least one additional agent is administered to the subject. In other embodiments, the composition comprising at least one additional agent can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the composition comprising at least one SCFA, for example as provided herein, or a molecule comprising a SCFA moiety, is administered to the subject.

PDE4 Inhibitors

In some embodiments, a method disclosed herein comprises administering to a subject in need thereof a composition comprising at least one SCFA, for example as provided herein, or a biologically-active derivative or precursor thereof, in combination with one or more phosphodiesterase 4 (PDE4) inhibitors. Non-limiting examples of PDE4 inhibitors include Apremilast (Otezla®), roflumilast (Daxas®), Crisaborole (5-(4-Cyanophenoxy)-2,3-dihydro-1-hydroxy-2,1-benzoxaborole, AN-2728, Eucrisa®), Pefcalcitol (M5181), and HFP034 (butyl 2-[2-(2-fluorophenyl) acetamido] benzoate). In some embodiments, a method disclosed herein comprises administering to a subject in need thereof a composition comprising at least one SCFA, for example as provided herein, or a biologically-active derivative or precursor thereof, and additionally one or more PDE4 inhibitors. In some embodiments, a method disclosed herein comprises administering to a subject in need thereof a composition comprising at least one SCFA, for example as provided herein, or a biologically-active derivative or precursor thereof, in combination with a composition comprising one or more PDE4 inhibitor.

Biologic Agents

In some embodiments, a method disclosed herein comprises administering to a subject in need thereof a composition comprising at least one SCFA, or a biologically-active derivative or precursor thereof, in combination with one or more biologic drugs. Nonlimiting biologic drugs include: etanercept (Enbrel®), infliximab (Remicade®), Apremilast (Otezla®), and adalimumab (Humira®). Additional nonlimiting examples of biologic drugs include: ustekinumab, secukinumab, ixekizumab, guselkumab, and risankizumab.

In some embodiments, a method disclosed herein comprises administering to a subject in need thereof a composition comprising at least one SCFA, for example as provided herein, or a biologically-active derivative or precursor thereof, and additionally one or more biologic agent. In some embodiments, a method disclosed herein comprises administering to a subject in need thereof a composition comprising at least one SCFA, for example as provided herein, or a biologically-active derivative or precursor thereof, in combination with a composition comprising one or more biologic agent.

Magnesium, Vitamin D, and Vitamin E

In some embodiments, a method disclosed herein comprises administering to a subject in need thereof a composition comprising at least one SCFA, for example as provided herein, or a biologically-active derivative or precursor thereof, and additionally one or more of magnesium or a source of magnesium, vitamin D (e.g., vitamin D3), and vitamin E (e.g., d-α-tocopherol acetate). Magnesium is a co-factor for more than 300 enzymes that regulate diverse biochemical reactions including regulation of blood glucose levels, detoxification, and others. Vitamin D3 deficiency is frequent in patients with immune disorders. Vitamin E has antioxidant activities. Non-limiting examples of a source of magnesium include magnesium chloride, magnesium hydroxide, magnesium carbonate, magnesium bicarbonate, magnesium sulfate, magnesium phosphate, and magnesium acetate.

In some embodiments, a method disclosed herein comprises administering to a subject in need thereof a composition comprising at least one SCFA, for example as provided herein, or a biologically-active derivative or precursor thereof, and additionally one or more of a source of magnesium, vitamin D (e.g., vitamin D3), and vitamin E. In some embodiments, a method disclosed herein comprises administering to a subject in need thereof a composition comprising at least one SCFA, for example as provided herein, or a biologically-active derivative or precursor thereof, in combination with a composition comprising one or more of a source of magnesium, vitamin D (e.g., vitamin D3), and vitamin E.

In some embodiments, a composition disclosed herein comprises a source of magnesium. In some embodiments, a composition disclosed herein comprises an inorganic magnesium salt such as magnesium chloride, magnesium carbonate, or magnesium phosphate. In some embodiments, a composition disclosed herein comprises vitamin D (e.g., vitamin D3). In some embodiments, a composition disclosed herein comprises vitamin E.

Pharmacodynamic and Pharmacokinetic Parameters

Pharmacokinetic and pharmacodynamic data can be obtained by various experimental techniques. Appropriate pharmacokinetic and pharmacodynamic profile components describing a particular composition can vary due to variations in the metabolism of compound of the disclosure in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A dose can be modulated to achieve a desired pharmacokinetic or pharmacodynamics profile, such as a desired or effective blood profile, as described herein. SC150 is a measure of the effectiveness of a substance in activating DNA binding by a protein target. This quantitative measure indicates the concentration of the compound required to increase the DNA binding activity by 50% relative to DNA binding activity in the absence of the compound.

The outcome of treating a human subject with a therapy can be measured by calculating pharmacodynamic and pharmacokinetic parameters. Non-limiting examples of pharmacodynamic and pharmacokinetic parameters that can be used to determine the effect of treatment of a subject with a therapy of the disclosure include: a) the amount of drug administered, which can be represented as a dose D; b) the dosing interval, which can be represented as $\tau$; c) the apparent volume in which a drug is distributed, which can be represented as a volume of distribution $V_d$, where $V_d = D/C_0$; d) the amount of drug in a given volume of tissue, which can be represented as concentration $C_0$ or $C_{ss}$, where $C_0$ or $C_{ss} = D/Vd$; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss}$. CL; h) the integral of the concentration-time curve after administration of a single dose, which can be represented as $AUC_{0-\infty}$ wherein $$\int_0^\infty C\,dt,$$

or in steady-state, which can be represented as $AUC\tau,_{ss}$, wherein $$\left(\int_t^{t+\pi} C\,dt; i\right)$$

the volume of tissue cleared of the drug per unit time, which can be represented as CL (clearance), wherein $CL=V_d.k_e=D/AUC$; j) the systemically available fraction of a drug, which can be represented as f, where $$f = \frac{AUCpo \cdot Div}{AUCiv \cdot Dpo};$$

k) the peak tissue concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as $$\% \ PTF = 100 \cdot \frac{(Cmax,\ ss - Cmin,\ ss)}{Cav,\ ss} \ \text{where} \ C_{av,ss} = \frac{AUC\tau,\ ss}{\tau}.$$

The pharmacokinetic parameters can be any parameters suitable for describing the tissue concentration profiles of a therapy of the disclosure. For example, the pharmacokinetics profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The $C_{max}$ can be, for example, not less than about 1 ng/ml; not less than about 2 ng/ml; not less than about 3 ng/ml; not less than about 4 ng/ml; not less than about 5 ng/mL; not less than about 6 ng/ml; not less than about 7 ng/ml; not less than about 8 ng/mL; not less than about 9 ng/ml; not less than about 10 ng/ml; not less than about 15 ng/ml; not less than about 20 ng/ml; not less than about 25 ng/ml; not less than about 50 ng/mL; not less than about 75 ng/ml; not less than about 100 ng/ml; not less than about 200 ng/ml; not than about 500 ng/mL; not than about 1,000 ng/mL; not than about 2,000 ng/ml; not less than about 3,000 ng/mL; not less than about 4,000 ng/mL; not less than about 5,000 ng/mL; not less than about 6,000 ng/ml; not less than about 7,000 ng/mL; not less than about 8,000 ng/ml; not less than about 9,000 ng/ml; not less than about 10,000 ng/ml; not less than about 12,500 ng/ml; not less than about 15,000 ng/ml; not less than about 17,500 ng/mL; not less than about 20,000 ng/ml; or any other $C_{max}$ appropriate for describing a pharmacokinetic profile of a compound described herein. The $C_{max}$ can be, for example, about 1 ng/mL to about 50,000 ng/ml; about 1 ng/mL to about 45,000 ng/mL; about 1 ng/mL to about 40,000 ng/mL; about 1 ng/mL to about 35,000 ng/ml; about 1 ng/mL to about 30,000 ng/mL; about 1 ng/mL to about 25,000 ng/ml; about 1 ng/mL to about 20,000 ng/ml; about 1 ng/mL to about 15,000 ng/ml; about 1 ng/mL to about 10,000 ng/mL; about 5,000 ng/ml to about 50,000 ng/ml; about 5,000 ng/mL to about 45,000 ng/ml; about 5,000 ng/mL to about 40,000 ng/ml; about 5,000 ng/mL to about 35,000 ng/ml; about 5,000 ng/mL to about 30,000 ng/ml; about 5,000 ng/ml to about 25,000 ng/ml; about 5,000 ng/mL to about 20,000 ng/ml; about 5,000 ng/mL to about 15,000 ng/ml; about 5,000 ng/mL to about 10,000 ng/ml; about 7,500 ng/mL to about 50,000 ng/mL; about 7,500 ng/mL to about 45,000 ng/mL; about 7,500 ng/mL to about 4,000 ng/ml; about 7,500 ng/mL to about 35,000 ng/ml; about 7,500 ng/mL to about 30,000 ng/ml; about 7,500 ng/ml to about 25,000 ng/mL; about 7,500 ng/mL to about 20,000 ng/mL; about 7,500 ng/ml to about 15,000 ng/ml; about 7,500 ng/mL to about 10,000 ng/mL; about 10,000 ng/mL to about 50,000 ng/ml; about 10,000 ng/mL to about 45,000 ng/ml; about 10,000 ng/mL to about 40,000 ng/mL; about 10,000 ng/ml to about 35,000 ng/mL; about 10,000 ng/mL to about 30,000 ng/ml; about 10,000 ng/mL to about 25,000 ng/ml; about 10,000 ng/mL to about 20,000 ng/ml; or about 10,000 ng/ml to about 15,000 ng/mL.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ or $AUC_{(last)}$ of a compound described herein can be, for example, not less than about 50,000 ng·hr/mL, not less than about 55,000 ng·hr/mL, not less than about 60,000 ng·hr/mL, not less than about 65,000 ng·hr/mL, not less than about 70,000 ng·hr/mL, not less than about 75,000 ng·hr/mL, not less than about 80,000 ng·hr/mL, not less than about 85,000 ng·hr/mL, not less than about 90,000 ng·hr/mL, not less than about 95,000 ng·hr/mL, not less than about 100,000 ng·hr/mL, not less than about 105,000 ng·hr/mL, not less than about 110,000 ng·hr/mL, not less than about 115,000 ng·hr/mL, not less than about 120,000 ng·hr/mL, not less than about 125,000 ng·hr/mL, not less than about 130,000 ng·hr/mL, not less than about 135,000 ng·hr/mL, not less than about 140,000 ng·hr/mL, not less than about 145,000 ng·hr/mL, not less than about 150,000 ng·hr/mL, not less than about 155,000 ng·hr/mL, not less than about 160,000 ng·hr/mL, not less than about 165,000 ng·hr/mL, not less than about 170,000 ng·hr/mL, not less than about 175,000 ng·hr/mL, not less than about 180,000 ng·hr/mL, not less than about 185,000 ng·hr/mL, not less than about 190,000 ng·hr/mL, not less than about 195,000 ng·hr/mL, not less than about 200,000 ng·hr/mL, or any other $AUC_{(0-inf)}$ appropriate for describing a pharmacokinetic profile of a compound described herein. The $AUC_{(0-inf)}$ of a compound described herein can be, for example, about 1,000 ng·hr/mL to about 100,000 ng·hr/mL; about 40,000 ng·hr/mL to about 50,000 ng·hr/mL; about 50,000 ng·hr/mL to about 60,000 ng·hr/mL; about 60,000 ng·hr/mL to about 70,000 ng·hr/mL; about 70,000 ng·hr/mL to about 80,000 ng·hr/mL; about 80,000 ng·hr/mL to about 90,000 ng·hr/mL; about 90,000 ng·hr/mL to about 100,000 ng·hr/mL; about 100,000 ng·hr/mL to about 125,000 ng·hr/mL; about 125,000 ng·hr/mL to about 150,000 ng·hr/mL; about 150,000 ng·hr/mL to about 175,000 ng·hr/mL; about 175,000 ng·hr/mL to about 200,000 ng·hr/mL; about 50,000 ng·hr/mL to about 70,000 ng·hr/mL; about 50,000 ng·hr/mL to about 60,000 ng·hr/mL; about 50,000 ng·hr/mL to about 80,000 ng·hr/mL; about 50,000 ng·hr/mL to about 100,000 ng·hr/mL; about 50,000 ng·hr/mL to about 110,000 ng·hr/mL; about 50,000 ng·hr/mL to about 120,000 ng·hr/mL; about 50,000 ng·hr/mL to about 130,000 ng·hr/mL; about 50,000 ng·hr/mL to about 140,000 ng·hr/mL; about 50,000 ng·hr/mL to about 150,000 ng·hr/mL; about 60,000 ng·hr/mL to about 110,000 ng·hr/mL; about 60,000 ng·hr/mL to about 120,000 ng·hr/mL; about 60,000 ng·hr/mL to about 130,000 ng·hr/mL; about 60,000 ng·hr/mL to about 140,000 ng·hr/mL; about 60,000 ng·hr/mL to about 150,000 ng·hr/mL, about 100,000 ng·hr/mL to about 110,000 ng·hr/mL; about 100,000 ng·hr/mL to about 120,000 ng·hr/mL; about 100,000 ng·hr/mL to about 130,000 ng·hr/mL; about 100,000 ng·hr/mL to about 140,000 ng·hr/mL; or about 100,000 ng·hr/mL to about 150,000 ng·hr/mL.

Any embodiments disclosed herein can be used in conjunction or individually. For example, any pharmaceutically-acceptable excipient, method, technique, solvent, or compound disclosed herein can be used together with any other pharmaceutically-acceptable excipient, method, technique, solvent, or compound disclosed herein to achieve any therapeutic result. Compounds, excipients, and other formulation components can be present at any amount, ratio, or percentage disclosed herein in any such formulation, and any such combination can be used therapeutically for any purpose described herein.

EXAMPLES

Example 1: Synthesis of Deuterated Short Chain Fatty Acids

Deuterium substituted compositions are synthesized using various methods. For example, synthesis of d-7 butyric acid is synthesized from butyric acid using heat, pressure, Pt/C catalysts, and NaOD in $D_2O$ as described below.

n-Hexanoic Acid-$d1_1$

A mixture of hexanoic acid (13 g, 111.99 mmol), 0.6 g of Pt/C (10 wt % of the substrate) and NaOD (4.6 g, 111.99 mmol, 40% in $D_2O$) in $D_2O$ (120 mL) is stirred under hydrothermal conditions for 2 cycles on each of 3 days at 220° C. in a Parr pressure reactor (600 mL size). After cooling, the reaction mixture is diluted with dichloromethane (200 mL) and the mixture is filtered through Celite to remove the catalyst. The Celite pad is washed with water and the filtrate acidified to pH 2. The aqueous phase is extracted with diethyl ether (100 mL×3) and the combined organic phases are dried over $Na_2SO_4$, filtered, and concentrated in vacuo to give an oily substance (e.g., 10.7 g, 75% yield, 97±2% D; $^2H$ NMR (102.6 MHz, CDCl3) δD 2.31 (2.00 D, br s), 1.59 (2.04 D, br s), 1.27 (4.06 D, br s) 0.85 (3.03 D, br s); Isotope distribution (ESI-MS, -ve mode): 69% d11, 31% $d1_0$).

n-Butanoic Acid-$d_7$

This compound is prepared according to various methods. For example, methods described above for n-hexanoic acid-$d1_1$ (e.g., 70% yield, 98±2% D; 2H NMR (102.6 MHz, CDCl3) δD 2.27 (1.93 D, br s), 1.59 (1.86 D, br s), 0.90 (3.00 D, br s); Isotope distribution (ESI-MS, -ve mode): 90% d7, 10% d6).

Example 2: Treatment of Skin Disorders with Short Chain Fatty Acids

Psoriasis is a chronic auto-inflammatory disease that causes raised, red, scaly patches to appear on the skin. Psoriasis can appear anywhere on the body, but typically affects the outside of the elbows, knees or scalp. Some patient report that psoriasis is itchy, burns, and stings. Psoriasis is associated with other serious health conditions, such as diabetes, heart disease, and depression.

SCFAs are given orally up to three times a day for at least 3 weeks. The dose schedule is one to two (1-2) capsules or tablets administered up to 3 times daily for 7 days to 4 weeks followed by one (1) capsule or tablet administered up to 3 times daily for several weeks to several months. Each capsule or tablet comprises (i) 1 mg to 1 g of butyric acid or a pharmaceutically-acceptable salt thereof, (ii) 25 mg to 200 mg of propionic acid or a pharmaceutically-acceptable salt thereof. Sodium, magnesium or calcium salts of butyrate are used for these treatments. Treatment results in disappearance of one or more psoriatic lesions. When treatment is discontinued, psoriasis skin lesions reappear. When treatments are started again, lesions disappear once more. Individuals with psoriasis taking the capsules orally for 3-4 weeks show marked improvement or complete resolution of skin lesions.

Example 3: Treatment of Skin Disorders with Short Chain Fatty Acids

Various assays are designed and tested in an ex vivo human skin psoriasis model (e.g., Genoskin's InflammaSkin® model). Assays include evaluations of various cytokines (e.g., IL-17A Gen B, IL-21, IL-22, IL-23, IFN-γ, and TNF-α), Hematoxylin & Eosin (H&E) staining (e.g., incidence of pyknosis, vacuolization, and epidermal/dermal detachment), K16 expression in the epidermis, and evaluations of anti-inflammatory activity.

InflammaSkin® Models Culture and Treatment

A total of 16 biopsies of 15 mm diameter are produced from a single donor. Two NativeSkin® models with 12/15 mm silicon rings are produced from the biopsies and cultured under cell culture conditions (37° C., 5% $CO_2$, max. humidity) for 7 days with 2 mL of standard NativeSkin® medium renewed every day. Fourteen InflammaSkin® models with 12/15 mm silicon rings are produced by inducing in situ activation and Th17/Th1 polarization of skin resident T cells with a proprietary cocktail, and cultured under cell culture conditions (37° C., 5% $CO_2$, max. humidity) for 7 days with 2 mL of InflammaSkin® culture medium renewed every day.

From Day 1 to Day 6, models are systemically treated with SCFAs, or topically treated with positive control 0.05% Betamethasone.

At Day 7, supernatants are collected and stored at −80° C. and skin models of all conditions are carefully unmolded. Skin biopsies are re-punched to eliminate the area under the silicon ring, fixed in 10% buffered formalin and processed for paraffin wax embedding.

IL-22 Release/ELISA Assay

Immunoassays are used, for example, enzyme linked immunosorbent assays (ELISA). IL-22 release in the supernatant is assessed using the ELISA Human IL-22 kit (Abcam, ref: ab216170). Sample and the standards are analyzed in duplicate. The analysis is carried out on control conditions to confirm the donor sample's response to T-cell activation and to the positive control, betamethasone. Plates are read on VICTOR Nivo Multimode Microplate Reader. Values are expressed in pg/mL. For each condition, single values, mean and SEM are plotted using GraphPad Prism. Statistical analysis is performed using a One Way ANOVA test.

On Day 7, donor sample's IL-22 levels are assessed for responsiveness to inflammation induction/T-cell activation. Reduction in inflammation is assessed, for example, by comparing IL-22 levels to the InflammaSkin® controls, on Day 7 with positive treatment control, betamethasone.

Histological Analysis—Hematoxylin & Eosin (H&E) Staining

Skin structure and integrity and viability are evaluated using Hematoxylin & Eosin (H&E) staining following treatment with Betamethasone or SCFAs. H&E analysis features include pyknosis and vacuolization (indicators of cell death), and epidermal/dermal separation. H&E staining is performed on 5 μm thickness paraffin-embedded skin cross-sections. Representative images are acquired at 40× magnification using a Leica DMil microscope for analysis of skin structure integrity and viability.

The untreated InflammaSkin® groups show reduced epidermal cellular viability, as indicated by pyknotic and vacuolized cells, and epidermal/dermal separation.

Betamethasone treatment of the InflammaSkin® models appear to reduce the incidence of vacuolization and epidermal/dermal separation. Evidence of a large amount of pyknosis, especially in the upper layers of the epidermis, is observed.

Systemic SCFA treatment of the InflammaSkin® models increases the health of the skin. Pyknosis/vacuolization of the epidermal layers closely resembled that of the untreated InflammaSkin® histological findings. Significantly less epidermal/dermal separation in the SCFA is observed in the treated vs untreated InflammaSkin® models, and suggests that the SCFA has some effect on preventing the degradation of the skin after inflammation induction.

Histological Analysis—Anti-K16 Immunostaining

K16, a type 1 keratin, is upregulated in hyperproliferative states, such as in psoriasis. Anti-K16 immunostaining is performed on 5 μm thickness paraffin-embedded skin cross-sections with a primary antibody anti-K16 (Sigma, SAB4501660, Rabbit IgG at 1/100 vol/vol dilution) and a secondary antibody (LifeTech, A21428 Alexa Fluor 647 at 1/500 vol/vol dilution). Representative pictures are acquired at 40× magnification using a Zeiss AxioImager M2 microscope for anti-K16 immunostaining Day 0 and Day 7 InflammaSkin® models. The Day 7 InflammaSkin® models show K16 is upregulated.

In InflammaSkin® models, K16 is upregulated in treated samples compared to the uninflamed, NativeSkin® controls where no to very little K16 is expressed. Some variability in the K16 expression is observed across the five replicates. K16 expression (besides Replicate 1) appears to be expressed almost uniformly from the basal to the corneum epidermal layers.

Betamethasone and SCFA decrease the expression of K16 in the epidermis. Expression of K16 in the basal/suprabasal epidermal layers is compared to expression in the upper layers of the epidermis (versus expressed throughout the epidermis).

Cytokine Analysis—Multiplex Assay

In the study, treatment with SCFAs attenuates inflammation by decreasing expression of a pro-inflammatory cytokine, such as tumor necrosis factor alpha, and/or stimulating the expression of an anti-inflammatory cytokine, such as interleukin-10.

Human pro-inflammatory cytokines released in the supernatant are quantified using the V-PLEX Human IL-17A Kit (MesoScale Discovery, reference: K151RFD-1) and V-PLEX Human TNFα Kit (MesoScale Discovery, reference: K151QWD-1). Values are expressed in pg/mL. For each condition, single values, mean and SEM are plotted using GraphPad Prism. Statistical analysis was performed using a One Way ANOVA test.

IL-17A is a cytokine upregulated both in psoriasis and in InflammaSkin® models. IL-17A expression is assessed following treatment with Betamethasone or SCFAs and compared to untreated InflammaSkin® models. SCFAs are more efficacious at reducing this cytokine level in the InflammaSkin® models than the betamethasone treatment.

TNF-α is a cytokine upregulated in psoriasis and slightly in InflammaSkin® models (Jardet et al, 2020 Exp Derm).

TNF-α expression is assessed following treatment with Betamethasone or SCFAs, and compared to untreated samples.

EMBODIMENTS

The following non-limiting embodiments provide illustrative examples of the disclosure, but do not limit the scope of the disclosure.

Embodiment 1. A pharmaceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) a solid pharmaceutically-acceptable excipient.

Embodiment 2. The pharmaceutical composition of embodiment 1, wherein the amount of butyric acid or the pharmaceutically-acceptable salt thereof is at least 10 mg.

Embodiment 3. The pharmaceutical composition of embodiment 1 or 2, wherein the amount of butyric acid or the pharmaceutically-acceptable salt thereof is at least 100 mg.

Embodiment 4. The pharmaceutical composition of any one of embodiments 1-3, wherein the amount of butyric acid or the pharmaceutically-acceptable salt thereof is at least 800 mg.

Embodiment 5. The pharmaceutical composition of any one of embodiments 1-4, the pharmaceutical composition comprising the pharmaceutically-acceptable salt of butyric acid, wherein the pharmaceutically-acceptable salt is sodium butyrate.

Embodiment 6. The pharmaceutical composition of any one of embodiments 1-5, wherein at least 5% of hydrogen atoms in the butyric acid or the pharmaceutically-acceptable salt thereof are deuterium.

Embodiment 7. The pharmaceutical composition of any one of embodiments 1-6, wherein at least 10% of hydrogen atoms in the butyric acid or the pharmaceutically-acceptable salt thereof are deuterium.

Embodiment 8. The pharmaceutical composition of any one of embodiments 1-7, wherein at least 25% of hydrogen atoms in the butyric acid or the pharmaceutically-acceptable salt thereof are deuterium.

Embodiment 9. The pharmaceutical composition of any one of embodiments 1-8, wherein at least 50% of hydrogen atoms in the butyric acid or the pharmaceutically-acceptable salt thereof are deuterium.

Embodiment 10. The pharmaceutical composition of any one of embodiments 1-9, wherein at least 75% of hydrogen atoms in the butyric acid or the pharmaceutically-acceptable salt thereof are deuterium.

Embodiment 11. The pharmaceutical composition of any one of embodiments 1-10, wherein at least 80% of hydrogen atoms in the butyric acid or the pharmaceutically-acceptable salt thereof are deuterium.

Embodiment 12. The pharmaceutical composition of any one of embodiments 1-11, wherein at least 85% of hydrogen atoms in the butyric acid or the pharmaceutically-acceptable salt thereof are deuterium.

Embodiment 13. The pharmaceutical composition of any one of embodiments 1-12, wherein at least 90% of hydrogen atoms in the butyric acid or the pharmaceutically-acceptable salt thereof are deuterium.

Embodiment 14. The pharmaceutical composition of any one of embodiments 1-13, wherein at least 95% of hydrogen atoms in the butyric acid or the pharmaceutically-acceptable salt thereof are deuterium.

Embodiment 15. The pharmaceutical composition of any one of embodiments 1-14, wherein at least 99% of hydrogen atoms in the butyric acid or the pharmaceutically-acceptable salt thereof are deuterium.

Embodiment 16. The pharmaceutical composition of any one of embodiments 1-15, wherein the solid pharmaceutically-acceptable excipient is a tablet filler.

Embodiment 17. The pharmaceutical composition of any one of embodiments 1-16, wherein the pharmaceutical composition is an oral form.

Embodiment 18. The pharmaceutical composition of any one of embodiments 1-17, wherein the pharmaceutical composition is a tablet.

Embodiment 19. The pharmaceutical composition of any one of embodiments 1-18, further comprising an amount of at least 1 mg of propionic acid or a pharmaceutically-acceptable salt thereof, wherein at least 1% of hydrogen atoms in the propionic acid or the pharmaceutically-acceptable salt thereof are deuterium.

Embodiment 20. The pharmaceutical composition of embodiment 19, wherein the amount of propionic acid or the pharmaceutically-acceptable salt thereof is at least 10 mg.

Embodiment 21. The pharmaceutical composition of embodiment 19 or 20, wherein the amount of propionic acid or the pharmaceutically-acceptable salt thereof is at least 25 mg.

Embodiment 22. The pharmaceutical composition of any one of embodiments 19-21, wherein the amount of propionic acid or the pharmaceutically-acceptable salt thereof is at least 40 mg.

Embodiment 23. The pharmaceutical composition of any one of embodiments 19-22, the pharmaceutical composition comprising the pharmaceutically-acceptable salt of propionic acid, wherein the pharmaceutically-acceptable salt is sodium propionate.

Embodiment 24. The pharmaceutical composition of any one of embodiments 19-23, wherein at least 5% of hydrogen atoms in the propionic acid or the pharmaceutically-acceptable salt thereof are deuterium.

Embodiment 25. The pharmaceutical composition of any one of embodiments 19-24, wherein at least 10% of hydrogen atoms in the propionic acid or the pharmaceutically-acceptable salt thereof are deuterium.

Embodiment 26. The pharmaceutical composition of any one of embodiments 19-25, wherein at least 25% of hydrogen atoms in the propionic acid or the pharmaceutically-acceptable salt thereof are deuterium.

Embodiment 27. The pharmaceutical composition of any one of embodiments 19-26, wherein at least 50% of hydrogen atoms in the propionic acid or the pharmaceutically-acceptable salt thereof are deuterium.

Embodiment 28. The pharmaceutical composition of any one of embodiments 19-27, wherein at least 75% of hydrogen atoms in the propionic acid or the pharmaceutically-acceptable salt thereof are deuterium.

Embodiment 29. The pharmaceutical composition of any one of embodiments 19-28, wherein at least 80% of hydrogen atoms in the propionic acid or the pharmaceutically-acceptable salt thereof are deuterium.

Embodiment 30. The pharmaceutical composition of any one of embodiments 19-29, wherein at least 85% of hydrogen atoms in the propionic acid or the pharmaceutically-acceptable salt thereof are deuterium.

Embodiment 31. The pharmaceutical composition of any one of embodiments 19-30, wherein at least 90% of hydrogen atoms in the propionic acid or the pharmaceutically-acceptable salt thereof are deuterium.

Embodiment 32. The pharmaceutical composition of any one of embodiments 19-31, wherein at least 95% of hydrogen atoms in the propionic acid or the pharmaceutically-acceptable salt thereof are deuterium.

Embodiment 33. The pharmaceutical composition of any one of embodiments 19-32, wherein at least 99% of hydrogen atoms in the propionic acid or the pharmaceutically-acceptable salt thereof are deuterium.

Embodiment 34. The pharmaceutical composition of any one of embodiments 1-33, further comprising a source of magnesium.

Embodiment 35. The pharmaceutical composition of any one of embodiments 1-34, further comprising magnesium chloride.

Embodiment 36. The pharmaceutical composition of any one of embodiments 1-35, further comprising vitamin D.

Embodiment 37. A pharmaceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and (b) a solid pharmaceutically-acceptable excipient.

Embodiment 38. The pharmaceutical composition of embodiment 37, wherein the amount of butyric acid or the pharmaceutically-acceptable salt of butyrate ion is at least 10 mg.

Embodiment 39. The pharmaceutical composition of embodiment 37 or 38, wherein the amount of butyric acid or the pharmaceutically-acceptable salt of butyrate ion is at least 100 mg.

Embodiment 40. The pharmaceutical composition of any one of embodiments 37-39, wherein the amount of butyric acid or the pharmaceutically-acceptable salt of butyrate ion is at least 800 mg.

Embodiment 41. The pharmaceutical composition of any one of embodiments 37-40, the pharmaceutical composition comprising the pharmaceutically-acceptable salt of butyrate ion, wherein the pharmaceutically-acceptable salt of butyrate ion is sodium butyrate.

Embodiment 42. The pharmaceutical composition of any one of embodiments 37-41, wherein the solid pharmaceutically-acceptable excipient is a tablet filler.

Embodiment 43. The pharmaceutical composition of any one of embodiments 37-42, wherein the pharmaceutical composition is an oral form.

Embodiment 44. The pharmaceutical composition of any one of embodiments 37-43, wherein the pharmaceutical composition is a tablet.

Embodiment 45. The pharmaceutical composition of any one of embodiments 37-44, wherein the butyric acid has an average molecular mass of 94 D to 96 D as determined by time-of-flight mass spectrometry, and the butyrate ion has an average molecular mass of 93 D to 95 D as determined by time-of-flight mass spectrometry.

Embodiment 46. The pharmaceutical composition of any one of embodiments 37-45, wherein the butyric acid has an average molecular mass of 94.8 D to 95.2 D as determined by time-of-flight mass spectrometry, and the butyrate ion has an average molecular mass of 93.8 D to 94.2 D as determined by time-of-flight mass spectrometry.

Embodiment 47. The pharmaceutical composition of any one of embodiments 37-46, further comprising an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry.

Embodiment 48. The pharmaceutical composition of embodiment 47, wherein the propionic acid has an average molecular mass of 78 D to 80 D as determined by time-of-flight mass spectrometry, and the propionate ion has an average molecular mass of 77 D to 79 D as determined by time-of-flight mass spectrometry.

Embodiment 49. The pharmaceutical composition of embodiment 47 or 48, wherein the propionic acid has an average molecular mass of 78.8 D to 79.2 D as determined by time-of-flight mass spectrometry, and the propionate ion has an average molecular mass of 77.8 D to 78.2 D as determined by time-of-flight mass spectrometry.

Embodiment 50. The pharmaceutical composition of any one of embodiments 47-49, wherein the amount of propionic acid or the pharmaceutically-acceptable salt thereof is at least 10 mg.

Embodiment 51. The pharmaceutical composition of any one of embodiments 47-50, wherein the amount of propionic acid or the pharmaceutically-acceptable salt thereof is at least 25 mg.

Embodiment 52. The pharmaceutical composition of any one of embodiments 47-51, wherein the amount of propionic acid or the pharmaceutically-acceptable salt thereof is at least 40 mg.

Embodiment 53. The pharmaceutical composition of any one of embodiments 47-52, the pharmaceutical composition comprising the pharmaceutically-acceptable salt of propionic acid, wherein the pharmaceutically-acceptable salt is sodium propionate.

Embodiment 54. The pharmaceutical composition of any one of embodiments 37-53, further comprising a source of magnesium.

Embodiment 55. The pharmaceutical composition of any one of embodiments 37-54, further comprising magnesium chloride.

Embodiment 56. The pharmaceutical composition of any one of embodiments 37-55, further comprising vitamin D.

Embodiment 57. A pharmaceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein:

$H^{a1}$ is a population of isotopes of hydrogen that is about a natural abundance of isotopes of hydrogen or a population of isotopes of hydrogen that is at least 1% deuterium;

$H^{b1}$ is a population of isotopes of hydrogen that is about a natural abundance of isotopes of hydrogen or a population of isotopes of hydrogen that is at least 1% deuterium;

$H^{c1}$ is a population of isotopes of hydrogen that is about a natural abundance of isotopes of hydrogen or a population of isotopes of hydrogen that is at least 1% deuterium;

$H^{d1}$ is a population of isotopes of hydrogen that is about a natural abundance of isotopes of hydrogen or a population of isotopes of hydrogen that is at least 1% deuterium;

$H^{e1}$ is a population of isotopes of hydrogen that is about a natural abundance of isotopes of hydrogen or a population of isotopes of hydrogen that is at least 1% deuterium;

$H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) a solid pharmaceutically-acceptable excipient.

Embodiment 58. The pharmaceutical composition of embodiment 57, wherein the amount of butyric acid or the pharmaceutically-acceptable salt thereof is at least 10 mg.

Embodiment 59. The pharmaceutical composition of embodiment 57 or 58, wherein the amount of butyric acid or the pharmaceutically-acceptable salt thereof is at least 100 mg.

Embodiment 60. The pharmaceutical composition of any one of embodiments 57-59, wherein the amount of butyric acid or the pharmaceutically-acceptable salt thereof is at least 800 mg.

Embodiment 61. The pharmaceutical composition of any one of embodiments 57-60, the pharmaceutical composition comprising the pharmaceutically-acceptable salt of butyric acid, wherein the pharmaceutically-acceptable salt is sodium butyrate.

Embodiment 62. The pharmaceutical composition of any one of embodiments 57-61, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 5% deuterium.

Embodiment 63. The pharmaceutical composition of any one of embodiments 57-62, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 10% deuterium.

Embodiment 64. The pharmaceutical composition of any one of embodiments 57-63, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 25% deuterium.

Embodiment 65. The pharmaceutical composition of any one of embodiments 57-64, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 50% deuterium.

Embodiment 66. The pharmaceutical composition of any one of embodiments 57-65, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 75% deuterium.

Embodiment 67. The pharmaceutical composition of any one of embodiments 57-66, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 80% deuterium.

Embodiment 68. The pharmaceutical composition of any one of embodiments 57-67, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 85% deuterium.

Embodiment 69. The pharmaceutical composition of any one of embodiments 57-68, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 90% deuterium.

Embodiment 70. The pharmaceutical composition of any one of embodiments 57-69, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 95% deuterium.

Embodiment 71. The pharmaceutical composition of any one of embodiments 57-70, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 99% deuterium.

Embodiment 72a. The pharmaceutical composition of any one of embodiments 57-61, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium.

Embodiment 72b. The pharmaceutical composition of any one of embodiments 57-61, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium.

Embodiment 73. The pharmaceutical composition of any one of embodiments 57-61, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 1% deuterium.

Embodiment 74. The pharmaceutical composition of any one of embodiments 57-61, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 5% deuterium.

Embodiment 75. The pharmaceutical composition of embodiment 72, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 5% deuterium.

Embodiment 76. The pharmaceutical composition of embodiment 73, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 5% deuterium.

Embodiment 77. The pharmaceutical composition of embodiment 74, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 50% deuterium.

Embodiment 78. The pharmaceutical composition of embodiment 75, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 50% deuterium.

Embodiment 79. The pharmaceutical composition of embodiment 76, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 50% deuterium.

Embodiment 80. The pharmaceutical composition of embodiment 77, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 95% deuterium.

Embodiment 81. The pharmaceutical composition of embodiment 78, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 95% deuterium.

Embodiment 82. The pharmaceutical composition of embodiment 79, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 95% deuterium.

Embodiment 83. The pharmaceutical composition of any one of embodiments 57-82, wherein the solid pharmaceutically-acceptable excipient is a tablet filler.

Embodiment 84. The pharmaceutical composition of any one of embodiments 57-83, wherein the pharmaceutical composition is an oral form.

Embodiment 85. The pharmaceutical composition of any one of embodiments 57-84, wherein the pharmaceutical composition is a tablet.

Embodiment 86. The pharmaceutical composition of any one of embodiments 57-85, further comprising an amount of at least 1 mg of: $(C(H^{a2})(H^{b2})(H^{c2}))$—$(C(H^{d2})(H^{e2}))$—COOH or a pharmaceutically-acceptable salt thereof, wherein:

$H^{a2}$ is a population of isotopes of hydrogen that is about a natural abundance of isotopes of hydrogen or a population of isotopes of hydrogen that is at least 5% deuterium;

$H^{b2}$ is a population of isotopes of hydrogen that is about a natural abundance of isotopes of hydrogen or a population of isotopes of hydrogen that is at least 5% deuterium;

$H^{c2}$ is a population of isotopes of hydrogen that is about a natural abundance of isotopes of hydrogen or a population of isotopes of hydrogen that is at least 5% deuterium;

$H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium.

Embodiment 87. The pharmaceutical composition of embodiment 86, wherein at least one of $H^{a2}$, $H^{b2}$, $H^{c2}$, $H^{d2}$, and $H^{e2}$ is a population of isotopes of hydrogen that is at least 5% deuterium.

Embodiment 88. The pharmaceutical composition of embodiment 86 or 87, wherein at least one of $H^{a2}$, $H^{b2}$, $H^{c2}$, $H^{d2}$, and $H^{e2}$ is a population of isotopes of hydrogen that is at least 10% deuterium.

Embodiment 89. The pharmaceutical composition of any one of embodiments 86-88, wherein at least one of $H^{a2}$, $H^{b2}$, $H^{c2}$, $H^{d2}$, and $H^{e2}$ is a population of isotopes of hydrogen that is at least 25% deuterium.

Embodiment 90. The pharmaceutical composition of any one of embodiments 86-89, wherein at least one of $H^{a2}$, $H^{b2}$, $H^{c2}$, $H^{d2}$, and $H^{e2}$ is a population of isotopes of hydrogen that is at least 50% deuterium.

Embodiment 91. The pharmaceutical composition of any one of embodiments 86-90, wherein at least one of $H^{a2}$, $H^{b2}$, $H^{c2}$, $H^{d2}$, and $H^{e2}$ is a population of isotopes of hydrogen that is at least 75% deuterium.

Embodiment 92. The pharmaceutical composition of any one of embodiments 86-91, wherein at least one of $H^{a2}$, $H^{b2}$, $H^{c2}$, $H^{d2}$, and $H^{e2}$ is a population of isotopes of hydrogen that is at least 80% deuterium.

Embodiment 93. The pharmaceutical composition of any one of embodiments 86-92, wherein at least one of $H^{a2}$, $H^{b2}$, $H^{c2}$, $H^{d2}$, and $H^{e2}$ is a population of isotopes of hydrogen that is at least 85% deuterium.

Embodiment 94. The pharmaceutical composition of any one of embodiments 86-93, wherein at least one of $H^{a2}$, $H^{b2}$, $H^{c2}$, $H^{d2}$, and $H^{e2}$ is a population of isotopes of hydrogen that is at least 90% deuterium.

Embodiment 95. The pharmaceutical composition of any one of embodiments 86-94, wherein at least one of $H^{a2}$, $H^{b2}$, $H^{c2}$, $H^{d2}$, and $H^{e2}$ is a population of isotopes of hydrogen that is at least 95% deuterium.

Embodiment 96. The pharmaceutical composition of any one of embodiments 86-95, wherein at least one of $H^{a2}$, $H^{b2}$, $H^{c2}$, $H^{d2}$, and $H^{e2}$ is a population of isotopes of hydrogen that is at least 99% deuterium.

Embodiment 97. The pharmaceutical composition of embodiment 86, wherein at least three of $H^{a2}$, $H^{b2}$, $H^{c2}$, $H^{d2}$, and $H^{e2}$ are each independently a population of isotopes of hydrogen that is at least 1% deuterium.

Embodiment 98. The pharmaceutical composition of embodiment 86, wherein each of $H^{a2}$, $H^{b2}$, $H^{c2}$, $H^{d2}$, and $H^{e2}$ is independently a population of isotopes of hydrogen that is at least 1% deuterium.

Embodiment 99. The pharmaceutical composition of embodiment 86, wherein at least three of $H^{a2}$, $H^{b2}$, $H^{c2}$, $H^{d2}$, and $H^{e2}$ are each independently a population of isotopes of hydrogen that is at least 5% deuterium.

Embodiment 100. The pharmaceutical composition of embodiment 86, wherein each of $H^{a2}$, $H^{b2}$, $H^{c2}$, $H^{d2}$, and $H^{e2}$ is independently a population of isotopes of hydrogen that is at least 5% deuterium.

Embodiment 101. The pharmaceutical composition of embodiment 86, wherein at least three of $H^{a2}$, $H^{b2}$, $H^{c2}$, $H^{d2}$, and $H^{e2}$ are each independently a population of isotopes of hydrogen that is at least 50% deuterium.

Embodiment 102. The pharmaceutical composition of embodiment 86, wherein each of $H^{a2}$, $H^{b2}$, $H^{c2}$, $H^{d2}$, and $H^{e2}$ is independently a population of isotopes of hydrogen that is at least 50% deuterium.

Embodiment 103. The pharmaceutical composition of embodiment 86, wherein at least three of $H^{a2}$, $H^{b2}$, $H^{c2}$, $H^{d2}$, and $H^{e2}$ are each independently a population of isotopes of hydrogen that is at least 95% deuterium.

Embodiment 104. The pharmaceutical composition of embodiment 86, wherein each of $H^{a2}$, $H^{b2}$, $H^{c2}$, $H^{d2}$, and $H^{e2}$ is independently a population of isotopes of hydrogen that is at least 95% deuterium.

Embodiment 105. The pharmaceutical composition of any one of embodiments 86-104, wherein the amount of propionic acid or the pharmaceutically-acceptable salt thereof is at least 10 mg.

Embodiment 106. The pharmaceutical composition of any one of embodiments 86-105, wherein the amount of propionic acid or the pharmaceutically-acceptable salt thereof is at least 25 mg.

Embodiment 107. The pharmaceutical composition of any one of embodiments 86-106, wherein the amount of propionic acid or the pharmaceutically-acceptable salt thereof is at least 40 mg.

Embodiment 108. The pharmaceutical composition of any one of embodiments 86-107, the pharmaceutical composition comprising the pharmaceutically-acceptable salt of propionic acid, wherein the pharmaceutically-acceptable salt is sodium propionate.

Embodiment 109. The pharmaceutical composition of any one of embodiments 57-108, further comprising a source of magnesium.

Embodiment 110. The pharmaceutical composition of any one of embodiments 57-109, further comprising magnesium chloride.

Embodiment 111. The pharmaceutical composition of any one of embodiments 57-110, further comprising vitamin D.

Embodiment 112. A pharmaceutical composition comprising: (a) an amount of at least 1 mg of propionic acid or a pharmaceutically-acceptable salt thereof, wherein at least 1% of hydrogen atoms in the propionic acid or the pharmaceutically-acceptable salt thereof are deuterium; and (b) a solid pharmaceutically-acceptable excipient.

Embodiment 113. The pharmaceutical composition of embodiment 112, wherein the amount of propionic acid or the pharmaceutically-acceptable salt thereof is at least 10 mg.

Embodiment 114. The pharmaceutical composition of embodiment 112 or 113, wherein the amount of propionic acid or the pharmaceutically-acceptable salt thereof is at least 25 mg.

Embodiment 115. The pharmaceutical composition of any one of embodiments 112-114, wherein the amount of propionic acid or the pharmaceutically-acceptable salt thereof is at least 40 mg.

Embodiment 116. The pharmaceutical composition of any one of embodiments 112-115, the pharmaceutical composition comprising the pharmaceutically-acceptable salt of propionic acid, wherein the pharmaceutically-acceptable salt is sodium propionate.

Embodiment 117. The pharmaceutical composition of any one of embodiments 112-116, wherein at least 5% of hydrogen atoms in the propionic acid or the pharmaceutically-acceptable salt thereof are deuterium.

Embodiment 118. The pharmaceutical composition of any one of embodiments 112-117, wherein at least 10% of hydrogen atoms in the propionic acid or the pharmaceutically-acceptable salt thereof are deuterium.

Embodiment 119. The pharmaceutical composition of any one of embodiments 112-118, wherein at least 25% of hydrogen atoms in the propionic acid or the pharmaceutically-acceptable salt thereof are deuterium.

Embodiment 120. The pharmaceutical composition of any one of embodiments 112-119, wherein at least 50% of hydrogen atoms in the propionic acid or the pharmaceutically-acceptable salt thereof are deuterium.

Embodiment 121. The pharmaceutical composition of any one of embodiments 112-120, wherein at least 75% of hydrogen atoms in the propionic acid or the pharmaceutically-acceptable salt thereof are deuterium.

Embodiment 122. The pharmaceutical composition of any one of embodiments 112-121, wherein at least 80% of hydrogen atoms in the propionic acid or the pharmaceutically-acceptable salt thereof are deuterium.

Embodiment 123. The pharmaceutical composition of any one of embodiments 112-122, wherein at least 85% of hydrogen atoms in the propionic acid or the pharmaceutically-acceptable salt thereof are deuterium.

Embodiment 124. The pharmaceutical composition of any one of embodiments 112-123, wherein at least 90% of hydrogen atoms in the propionic acid or the pharmaceutically-acceptable salt thereof are deuterium.

Embodiment 125. The pharmaceutical composition of any one of embodiments 112-124, wherein at least 95% of hydrogen atoms in the propionic acid or the pharmaceutically-acceptable salt thereof are deuterium.

Embodiment 126. The pharmaceutical composition of any one of embodiments 112-125, wherein at least 99% of hydrogen atoms in the propionic acid or the pharmaceutically-acceptable salt thereof are deuterium.

Embodiment 127. The pharmaceutical composition of any one of embodiments 112-126, wherein the solid pharmaceutically-acceptable excipient is a tablet filler.

Embodiment 128. The pharmaceutical composition of any one of embodiments 112-127, wherein the pharmaceutical composition is an oral form.

Embodiment 129. The pharmaceutical composition of any one of embodiments 112-128, wherein the pharmaceutical composition is a tablet.

Embodiment 130. The pharmaceutical composition of any one of embodiments 112-129, further comprising a source of magnesium.

Embodiment 131. The pharmaceutical composition of any one of embodiments 112-130, further comprising magnesium chloride.

Embodiment 132. The pharmaceutical composition of any one of embodiments 112-131, further comprising vitamin D.

Embodiment 133. A pharmaceutical composition comprising: (a) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry; and (b) a solid pharmaceutically-acceptable excipient.

Embodiment 134. The pharmaceutical composition of embodiment 133, wherein the propionic acid has an average molecular mass of 78 D to 80 D as determined by time-of-flight mass spectrometry, and the propionate ion has an average molecular mass of 77 D to 79 D as determined by time-of-flight mass spectrometry.

Embodiment 135. The pharmaceutical composition of embodiment 133 or 134, wherein the propionic acid has an average molecular mass of 78.8 D to 79.2 D as determined by time-of-flight mass spectrometry, and the propionate ion has an average molecular mass of 77.8 D to 78.2 D as determined by time-of-flight mass spectrometry.

Embodiment 136. The pharmaceutical composition of any one of embodiments 133-135, wherein the amount of propionic acid or the pharmaceutically-acceptable salt thereof is at least 10 mg.

Embodiment 137. The pharmaceutical composition of any one of embodiments 133-136, wherein the amount of propionic acid or the pharmaceutically-acceptable salt thereof is at least 25 mg.

Embodiment 138. The pharmaceutical composition of any one of embodiments 133-137, wherein the amount of propionic acid or the pharmaceutically-acceptable salt thereof is at least 40 mg.

Embodiment 139. The pharmaceutical composition of any one of embodiments 133-138, wherein the solid pharmaceutically-acceptable excipient is a tablet filler.

Embodiment 140. The pharmaceutical composition of any one of embodiments 133-139, wherein the pharmaceutical composition is an oral form.

Embodiment 141. The pharmaceutical composition of any one of embodiments 133-140, wherein the pharmaceutical composition is a tablet.

Embodiment 142. The pharmaceutical composition of any one of embodiments 133-141, the pharmaceutical composition comprising the pharmaceutically-acceptable salt of propionic acid, wherein the pharmaceutically-acceptable salt is sodium propionate.

Embodiment 143. The pharmaceutical composition of any one of embodiments 133-142, further comprising a source of magnesium.

Embodiment 144. The pharmaceutical composition of any one of embodiments 133-143, further comprising magnesium chloride.

Embodiment 145. The pharmaceutical composition of any one of embodiments 133-144, further comprising vitamin D.

Embodiment 146. A pharmaceutical composition comprising: (a) an amount of at least 1 mg of: $(C(H^{a2})(H^{b2})(H^{c2}))$—$(C(H^{d2})(H^{e2}))$—COOH or a pharmaceutically-acceptable salt thereof, wherein:

$H^{a2}$ is a population of isotopes of hydrogen that is about a natural abundance of isotopes of hydrogen or a population of isotopes of hydrogen that is at least 5% deuterium;

$H^{b2}$ is a population of isotopes of hydrogen that is about a natural abundance of isotopes of hydrogen or a population of isotopes of hydrogen that is at least 5% deuterium;

$H^{c2}$ is a population of isotopes of hydrogen that is about a natural abundance of isotopes of hydrogen or a population of isotopes of hydrogen that is at least 5% deuterium;

$H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium; and (b) a solid pharmaceutically-acceptable excipient.

Embodiment 147. The pharmaceutical composition of embodiment 146, wherein at least one of $H^{a2}$, $H^{b2}$, $H^{c2}$, $H^{d2}$, and $H^{e2}$ is a population of isotopes of hydrogen that is at least 5% deuterium.

Embodiment 148. The pharmaceutical composition of embodiment 146 or 147, wherein at least one of $H^{a2}$, $H^{b2}$, $H^{c2}$, $H^{d2}$, and $H^{e2}$ is a population of isotopes of hydrogen that is at least 10% deuterium.

Embodiment 149. The pharmaceutical composition of any one of embodiments 146-148, wherein at least one of $H^{a2}$, $H^{b2}$, $H^{c2}$, $H^{d2}$, and $H^{e2}$ is a population of isotopes of hydrogen that is at least 25% deuterium.

Embodiment 150. The pharmaceutical composition of any one of embodiments 146-149, wherein at least one of $H^{a2}$, $H^{b2}$, $H^{c2}$, $H^{d2}$, and $H^{e2}$ is a population of isotopes of hydrogen that is at least 50% deuterium.

Embodiment 151. The pharmaceutical composition of any one of embodiments 146-150, wherein at least one of $H^{a2}$, $H^{b2}$, $H^{c2}$, $H^{d2}$, and $H^{e2}$ is a population of isotopes of hydrogen that is at least 75% deuterium.

Embodiment 152. The pharmaceutical composition of any one of embodiments 146-151, wherein at least one of $H^{a2}$, $H^{b2}$, $H^{c2}$, $H^{d2}$, and $H^{e2}$ is a population of isotopes of hydrogen that is at least 80% deuterium.

Embodiment 153. The pharmaceutical composition of any one of embodiments 146-152, wherein at least one of $H^{a2}$, $H^{b2}$, $H^{c2}$, $H^{d2}$, and $H^{e2}$ is a population of isotopes of hydrogen that is at least 85% deuterium.

Embodiment 154. The pharmaceutical composition of any one of embodiments 146-153, wherein at least one of $H^{a2}$, $H^{b2}$, $H^{c2}$, $H^{d2}$, and $H^{e2}$ is a population of isotopes of hydrogen that is at least 90% deuterium.

Embodiment 155. The pharmaceutical composition of any one of embodiments 146-154, wherein at least one of $H^{a2}$, $H^{b2}$, $H^{c2}$, $H^{d2}$, and $H^{e2}$ is a population of isotopes of hydrogen that is at least 95% deuterium.

Embodiment 156. The pharmaceutical composition of any one of embodiments 146-155, wherein at least one of $H^{a2}$, $H^{b2}$, $H^{c2}$, $H^{d2}$, and $H^{e2}$ is a population of isotopes of hydrogen that is at least 99% deuterium.

Embodiment 157. The pharmaceutical composition of any one of embodiments 146-156, wherein at least three of $H^{a2}$, $H^{b2}$, $H^{c2}$, $H^{d2}$, and $H^{e2}$ are each independently a population of isotopes of hydrogen that is at least 1% deuterium.

Embodiment 158. The pharmaceutical composition of any one of embodiments 146-157, wherein each of $H^{a2}$, $H^{b2}$, $H^{c2}$, $H^{d2}$, and $H^{e2}$ is independently a population of isotopes of hydrogen that is at least 1% deuterium.

Embodiment 159. The pharmaceutical composition of embodiment 157, wherein at least three of $H^{a2}$, $H^{b2}$, $H^{c2}$, $H^{d2}$, and $H^{e2}$ are each independently a population of isotopes of hydrogen that is at least 5% deuterium.

Embodiment 160. The pharmaceutical composition of embodiment 157, wherein each of $H^{a2}$, $H^{b2}$, $H^{c2}$, $H^{d2}$, and $H^{e2}$ is independently a population of isotopes of hydrogen that is at least 5% deuterium.

Embodiment 161. The pharmaceutical composition of embodiment 157, wherein at least three of $H^{a2}$, $H^{b2}$, $H^{c2}$, $H^{d2}$, and $H^{e2}$ are each independently a population of isotopes of hydrogen that is at least 50% deuterium.

Embodiment 162. The pharmaceutical composition of embodiment 157, wherein each of $H^{a2}$, $H^{b2}$, $H^{c2}$, $H^{d2}$, and $H^{e2}$ is independently a population of isotopes of hydrogen that is at least 50% deuterium.

Embodiment 163. The pharmaceutical composition of embodiment 157, wherein at least three of $H^{a2}$, $H^{b2}$, $H^{c2}$, $H^{d2}$, and $H^{e2}$ are each independently a population of isotopes of hydrogen that is at least 95% deuterium.

Embodiment 164. The pharmaceutical composition of embodiment 157, wherein each of $H^{a2}$, $H^{b2}$, $H^{c2}$, $H^{d2}$, and $H^{e2}$ is independently a population of isotopes of hydrogen that is at least 95% deuterium.

Embodiment 165. The pharmaceutical composition of any one of embodiments 146-164, wherein the amount of propionic acid or the pharmaceutically-acceptable salt thereof is at least 10 mg.

Embodiment 166. The pharmaceutical composition of any one of embodiments 146-165, wherein the amount of propionic acid or the pharmaceutically-acceptable salt thereof is at least 25 mg.

Embodiment 167. The pharmaceutical composition of any one of embodiments 146-166, wherein the amount of propionic acid or the pharmaceutically-acceptable salt thereof is at least 40 mg.

Embodiment 168. The pharmaceutical composition of any one of embodiments 146-167, wherein the solid pharmaceutically-acceptable excipient is a tablet filler.

Embodiment 169. The pharmaceutical composition of any one of embodiments 146-168, wherein the pharmaceutical composition is an oral form.

Embodiment 170. The pharmaceutical composition of any one of embodiments 146-169, wherein the pharmaceutical composition is a tablet.

Embodiment 171. The pharmaceutical composition of any one of embodiments 146-170, the pharmaceutical composition comprising the pharmaceutically-acceptable salt of propionic acid, wherein the pharmaceutically-acceptable salt is sodium propionate.

Embodiment 172. The pharmaceutical composition of any one of embodiments 146-171, further comprising a source of magnesium.

Embodiment 173. The pharmaceutical composition of any one of embodiments 146-172, further comprising magnesium chloride.

Embodiment 174. The pharmaceutical composition of any one of embodiments 146-173, further comprising vitamin D.

Embodiment 175. A pharmaceutical composition comprising: (a) an amount of at least 1 mg of butyric acid or a pharmaceutically-acceptable salt thereof, wherein at least 1% of hydrogen atoms in the butyric acid or the pharmaceutically-acceptable salt thereof are deuterium; and (b) an amount of at least 1 mg of propionic acid or a pharmaceutically-acceptable salt thereof, wherein at least 1% of hydrogen atoms in the propionic acid or the pharmaceutically-acceptable salt thereof are deuterium.

Embodiment 176. The pharmaceutical composition of embodiment 175, wherein the amount of butyric acid or the pharmaceutically-acceptable salt thereof is at least 10 mg.

Embodiment 177. The pharmaceutical composition of embodiment 175 or 176, wherein the amount of butyric acid or the pharmaceutically-acceptable salt thereof is at least 100 mg.

Embodiment 178. The pharmaceutical composition of any one of embodiments 175-177, wherein the amount of butyric acid or the pharmaceutically-acceptable salt thereof is at least 800 mg.

Embodiment 179. The pharmaceutical composition of any one of embodiments 175-178, the pharmaceutical composition comprising the pharmaceutically-acceptable salt of butyric acid, wherein the pharmaceutically-acceptable salt is sodium butyrate.

Embodiment 180. The pharmaceutical composition of any one of embodiments 175-179, wherein at least 5% of hydrogen atoms in the butyric acid or the pharmaceutically-acceptable salt thereof are deuterium.

Embodiment 181. The pharmaceutical composition of any one of embodiments 175-180, wherein at least 10% of hydrogen atoms in the butyric acid or the pharmaceutically-acceptable salt thereof are deuterium.

Embodiment 182. The pharmaceutical composition of any one of embodiments 175-181, wherein at least 25% of hydrogen atoms in the butyric acid or the pharmaceutically-acceptable salt thereof are deuterium.

Embodiment 183. The pharmaceutical composition of any one of embodiments 175-182, wherein at least 50% of hydrogen atoms in the butyric acid or the pharmaceutically-acceptable salt thereof are deuterium.

Embodiment 184. The pharmaceutical composition of any one of embodiments 175-183, wherein at least 75% of hydrogen atoms in the butyric acid or the pharmaceutically-acceptable salt thereof are deuterium.

Embodiment 185. The pharmaceutical composition of any one of embodiments 175-184, wherein at least 80% of hydrogen atoms in the butyric acid or the pharmaceutically-acceptable salt thereof are deuterium.

Embodiment 186. The pharmaceutical composition of any one of embodiments 175-185, wherein at least 85% of hydrogen atoms in the butyric acid or the pharmaceutically-acceptable salt thereof are deuterium.

Embodiment 187. The pharmaceutical composition of any one of embodiments 175-186, wherein at least 90% of hydrogen atoms in the butyric acid or the pharmaceutically-acceptable salt thereof are deuterium.

Embodiment 188. The pharmaceutical composition of any one of embodiments 175-187, wherein at least 95% of hydrogen atoms in the butyric acid or the pharmaceutically-acceptable salt thereof are deuterium.

Embodiment 189. The pharmaceutical composition of any one of embodiments 175-188, wherein at least 99% of hydrogen atoms in the butyric acid or the pharmaceutically-acceptable salt thereof are deuterium.

Embodiment 190. The pharmaceutical composition of any one of embodiments 175-189, wherein the amount of propionic acid or the pharmaceutically-acceptable salt thereof is at least 10 mg.

Embodiment 191. The pharmaceutical composition of any one of embodiments 175-190, wherein the amount of propionic acid or the pharmaceutically-acceptable salt thereof is at least 25 mg.

Embodiment 192. The pharmaceutical composition of any one of embodiments 175-191, wherein the amount of propionic acid or the pharmaceutically-acceptable salt thereof is at least 40 mg.

Embodiment 193. The pharmaceutical composition of any one of embodiments 175-192, the pharmaceutical composition comprising the pharmaceutically-acceptable salt of propionic acid, wherein the pharmaceutically-acceptable salt is sodium propionate.

Embodiment 194. The pharmaceutical composition of any one of embodiments 175-193, wherein at least 5% of hydrogen atoms in the propionic acid or the pharmaceutically-acceptable salt thereof are deuterium.

Embodiment 195. The pharmaceutical composition of any one of embodiments 175-194, wherein at least 10% of hydrogen atoms in the propionic acid or the pharmaceutically-acceptable salt thereof are deuterium.

Embodiment 196. The pharmaceutical composition of any one of embodiments 175-195, wherein at least 25% of hydrogen atoms in the propionic acid or the pharmaceutically-acceptable salt thereof are deuterium.

Embodiment 197. The pharmaceutical composition of any one of embodiments 175-196, wherein at least 50% of hydrogen atoms in the propionic acid or the pharmaceutically-acceptable salt thereof are deuterium.

Embodiment 198. The pharmaceutical composition of any one of embodiments 175-197, wherein at least 75% of hydrogen atoms in the propionic acid or the pharmaceutically-acceptable salt thereof are deuterium.

Embodiment 199. The pharmaceutical composition of any one of embodiments 175-198, wherein at least 80% of hydrogen atoms in the propionic acid or the pharmaceutically-acceptable salt thereof are deuterium.

Embodiment 200. The pharmaceutical composition of any one of embodiments 175-199, wherein at least 85% of hydrogen atoms in the propionic acid or the pharmaceutically-acceptable salt thereof are deuterium.

Embodiment 201. The pharmaceutical composition of any one of embodiments 175-200, wherein at least 90% of hydrogen atoms in the propionic acid or the pharmaceutically-acceptable salt thereof are deuterium.

Embodiment 202. The pharmaceutical composition of any one of embodiments 175-201, wherein at least 95% of hydrogen atoms in the propionic acid or the pharmaceutically-acceptable salt thereof are deuterium.

Embodiment 203. The pharmaceutical composition of any one of embodiments 175-202, wherein at least 99% of hydrogen atoms in the propionic acid or the pharmaceutically-acceptable salt thereof are deuterium.

Embodiment 204. The pharmaceutical composition of any one of embodiments 175-203, further comprising a source of magnesium.

Embodiment 205. The pharmaceutical composition of any one of embodiments 175-204, further comprising magnesium chloride.

Embodiment 206. The pharmaceutical composition of any one of embodiments 175-205, further comprising vitamin D.

Embodiment 207. The pharmaceutical composition of any one of embodiments 175-206, wherein the pharmaceutical composition is an oral form.

Embodiment 208. The pharmaceutical composition of any one of embodiments 175-207, wherein the pharmaceutical composition is a tablet.

Embodiment 209. A pharmaceutical composition comprising: (a) an amount of at least 1 mg of butyric acid or a pharmaceutically-acceptable salt of butyrate ion, wherein the butyric acid has an average molecular mass of 93 D to 97 D as determined by time-of-flight mass spectrometry, and the butyrate ion has an average molecular mass of 92 D to 96 D as determined by time-of-flight mass spectrometry; and (b) an amount of at least 1 mg of propionic acid or a pharmaceutically-acceptable salt of propionate ion, wherein the propionic acid has an average molecular mass of 77 D to 81 D as determined by time-of-flight mass spectrometry, and the propionate ion has an average molecular mass of 76 D to 80 D as determined by time-of-flight mass spectrometry.

Embodiment 210. The pharmaceutical composition of embodiment 209, wherein the amount of butyric acid or the pharmaceutically-acceptable salt of butyrate ion is at least 10 mg.

Embodiment 211. The pharmaceutical composition of embodiment 209 or 210, wherein the amount of butyric acid or the pharmaceutically-acceptable salt of butyrate ion is at least 100 mg.

Embodiment 212. The pharmaceutical composition of any one of embodiments 209-211, wherein the amount of butyric acid or the pharmaceutically-acceptable salt of butyrate ion is at least 800 mg.

Embodiment 213. The pharmaceutical composition of any one of embodiments 209-212, the pharmaceutical composition comprising the pharmaceutically-acceptable salt of butyrate ion, wherein the pharmaceutically-acceptable salt of butyrate ion is sodium butyrate.

Embodiment 214. The pharmaceutical composition of any one of embodiments 209-213, wherein the butyric acid has an average molecular mass of 94 D to 96 D as determined by time-of-flight mass spectrometry, and the butyrate ion has an average molecular mass of 93 D to 95 D as determined by time-of-flight mass spectrometry.

Embodiment 215. The pharmaceutical composition of any one of embodiments 209-214, wherein the butyric acid has an average molecular mass of 94.8 D to 95.2 D as determined by time-of-flight mass spectrometry, and the butyrate ion has an average molecular mass of 93.8 D to 94.2 D as determined by time-of-flight mass spectrometry.

Embodiment 216. The pharmaceutical composition of any one of embodiments 209-215, wherein the propionic acid has an average molecular mass of 78 D to 80 D as determined by time-of-flight mass spectrometry, and the propionate ion has an average molecular mass of 77 D to 79 D as determined by time-of-flight mass spectrometry.

Embodiment 217. The pharmaceutical composition of any one of embodiments 209-216, wherein the propionic acid has an average molecular mass of 78.8 D to 79.2 D as determined by time-of-flight mass spectrometry, and the propionate ion has an average molecular mass of 77.8 D to 78.2 D as determined by time-of-flight mass spectrometry.

Embodiment 218. The pharmaceutical composition of any one of embodiments 209-217, wherein the amount of propionic acid or the pharmaceutically-acceptable salt thereof is at least 10 mg.

Embodiment 219. The pharmaceutical composition of any one of embodiments 209-218, wherein the amount of propionic acid or the pharmaceutically-acceptable salt thereof is at least 25 mg.

Embodiment 220. The pharmaceutical composition of any one of embodiments 209-219, wherein the amount of propionic acid or the pharmaceutically-acceptable salt thereof is at least 40 mg.

Embodiment 221. The pharmaceutical composition of any one of embodiments 209-220, the pharmaceutical composition comprising the pharmaceutically-acceptable salt of propionic acid, wherein the pharmaceutically-acceptable salt is sodium propionate.

Embodiment 222. The pharmaceutical composition of any one of embodiments 209-221, further comprising a source of magnesium.

Embodiment 223. The pharmaceutical composition of any one of embodiments 209-222, further comprising magnesium chloride.

Embodiment 224. The pharmaceutical composition of any one of embodiments 209-223, further comprising vitamin D.

Embodiment 225. The pharmaceutical composition of any one of embodiments 209-224, wherein the pharmaceutical composition is an oral form.

Embodiment 226. The pharmaceutical composition of any one of embodiments 209-225, wherein the pharmaceutical composition is a tablet.

Embodiment 227. A pharmaceutical composition comprising: (a) an amount of at least 1 mg of: $(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein:

$H^{a1}$ is a population of isotopes of hydrogen that is about a natural abundance of isotopes of hydrogen or a population of isotopes of hydrogen that is at least 1% deuterium;

$H^{b1}$ is a population of isotopes of hydrogen that is about a natural abundance of isotopes of hydrogen or a population of isotopes of hydrogen that is at least 1% deuterium;

$H^{e1}$ is a population of isotopes of hydrogen that is about a natural abundance of isotopes of hydrogen or a population of isotopes of hydrogen that is at least 1% deuterium;

$H^{d1}$ is a population of isotopes of hydrogen that is about a natural abundance of isotopes of hydrogen or a population of isotopes of hydrogen that is at least 1% deuterium;

$H^{e1}$ is a population of isotopes of hydrogen that is about a natural abundance of isotopes of hydrogen or a population of isotopes of hydrogen that is at least 1% deuterium;

$H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and (b) an amount of at least 1 mg of: $(C(H^{a2})(H^{b2})(H^{c2}))$—$(C(H^{d2})(H^{e2}))$—COOH or a pharmaceutically-acceptable salt thereof, wherein:

$H^{a2}$ is a population of isotopes of hydrogen that is about a natural abundance of isotopes of hydrogen or a population of isotopes of hydrogen that is at least 5% deuterium;

$H^{b2}$ is a population of isotopes of hydrogen that is about a natural abundance of isotopes of hydrogen or a population of isotopes of hydrogen that is at least 5% deuterium;

$H^{c2}$ is a population of isotopes of hydrogen that is about a natural abundance of isotopes of hydrogen or a population of isotopes of hydrogen that is at least 5% deuterium;

$H^{d2}$ is a population of isotopes of hydrogen that is about a natural abundance of isotopes of hydrogen or a population of isotopes of hydrogen that is at least 5% deuterium; and $H^{e2}$ is a population of isotopes of hydrogen that is about a natural abundance of isotopes of hydrogen or a population of isotopes of hydrogen that is at least 5% deuterium, wherein at least one of $H^{a2}$, $H^{b2}$, $H^{c2}$, $H^{d2}$, and $H^{e2}$ is a population of isotopes of hydrogen that is at least 5% deuterium.

Embodiment 228. The pharmaceutical composition of embodiment 227, wherein the amount of butyric acid or the pharmaceutically-acceptable salt thereof is at least 10 mg.

Embodiment 229. The pharmaceutical composition of embodiment 227 and 228, wherein the amount of butyric acid or the pharmaceutically-acceptable salt thereof is at least 100 mg.

Embodiment 230. The pharmaceutical composition of any one of embodiments 227-229, wherein the amount of butyric acid or the pharmaceutically-acceptable salt thereof is at least 800 mg.

Embodiment 231. The pharmaceutical composition of any one of embodiments 227-230, the pharmaceutical composition comprising the pharmaceutically-acceptable salt of butyric acid, wherein the pharmaceutically-acceptable salt is sodium butyrate.

Embodiment 232. The pharmaceutical composition of any one of embodiments 227-231, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 5% deuterium.

Embodiment 233. The pharmaceutical composition of any one of embodiments 227-232, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 10% deuterium.

Embodiment 234. The pharmaceutical composition of any one of embodiments 227-233, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 25% deuterium.

Embodiment 235. The pharmaceutical composition of any one of embodiments 227-234, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 50% deuterium.

Embodiment 236. The pharmaceutical composition of any one of embodiments 227-235, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 75% deuterium.

Embodiment 237. The pharmaceutical composition of any one of embodiments 227-236, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 80% deuterium.

Embodiment 238. The pharmaceutical composition of any one of embodiments 227-237, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 85% deuterium.

Embodiment 239. The pharmaceutical composition of any one of embodiments 227-238, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 90% deuterium.

Embodiment 240. The pharmaceutical composition of any one of embodiments 227-239, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 95% deuterium.

Embodiment 241. The pharmaceutical composition of any one of embodiments 227-240, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 99% deuterium.

Embodiment 242. The pharmaceutical composition of any one of embodiments 227-241, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium.

Embodiment 243. The pharmaceutical composition of any one of embodiments 227-242, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium.

Embodiment 244. The pharmaceutical composition of any one of embodiments 227-243, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 1% deuterium.

Embodiment 245. The pharmaceutical composition of embodiment 242, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 5% deuterium.

Embodiment 246. The pharmaceutical composition of embodiment 243, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 5% deuterium.

Embodiment 247. The pharmaceutical composition of embodiment 244, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 5% deuterium.

Embodiment 248. The pharmaceutical composition of embodiment 245, wherein at least three of $H^{a1}$, $H^{b1}$, $H^{c1}$, $H^{d1}$, $H^{e1}$, $H^{f1}$, and $H^{f1}$ are each independently a population of isotopes of hydrogen that is at least 50% deuterium.

Embodiment 249. The pharmaceutical composition of embodiment 246, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 50% deuterium.

Embodiment 250. The pharmaceutical composition of embodiment 247, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 50% deuterium.

Embodiment 251. The pharmaceutical composition of embodiment 248, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 95% deuterium.

Embodiment 252. The pharmaceutical composition of embodiment 249, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 95% deuterium.

Embodiment 253. The pharmaceutical composition of embodiment 250, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 95% deuterium.

Embodiment 254. The pharmaceutical composition of any one of embodiments 227-253, wherein the amount of propionic acid or the pharmaceutically-acceptable salt thereof is at least 10 mg.

Embodiment 255. The pharmaceutical composition of any one of embodiments 227-254, wherein the amount of propionic acid or the pharmaceutically-acceptable salt thereof is at least 25 mg.

Embodiment 256. The pharmaceutical composition of any one of embodiments 227-254, wherein the amount of propionic acid or the pharmaceutically-acceptable salt thereof is at least 40 mg.

Embodiment 257. The pharmaceutical composition of any one of embodiments 227-256, the pharmaceutical composition comprising the pharmaceutically-acceptable salt of propionic acid, wherein the pharmaceutically-acceptable salt is sodium propionate.

Embodiment 258. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 5% deuterium.

Embodiment 259. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 10% deuterium.

Embodiment 260. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 25% deuterium.

Embodiment 261. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 50% deuterium.

Embodiment 262. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 75% deuterium.

Embodiment 263. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 80% deuterium.

Embodiment 264. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 85% deuterium.

Embodiment 265. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 90% deuterium.

Embodiment 266. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 95% deuterium.

Embodiment 267. The pharmaceutical composition of any one of embodiments 227-257, wherein at least one of $H^{a2}$, $H^{b2}$, $H^{c2}$, $H^{d2}$, and $H^{e2}$ is a population of isotopes of hydrogen that is at least 99% deuterium.

Embodiment 268. The pharmaceutical composition of any one of embodiments 227-257, wherein at least three of $H^{a2}$, $H^{b2}$, $H^{c2}$, $H^{d2}$, and $H^{e2}$ are each independently a population of isotopes of hydrogen that is at least 1% deuterium.

Embodiment 269. The pharmaceutical composition of any one of embodiments 227-257, wherein each of $H^{a2}$, $H^{b2}$, $H^{c2}$, $H^{d2}$, and $H^{e2}$ is independently a population of isotopes of hydrogen that is at least 1% deuterium.

Embodiment 270. The pharmaceutical composition of embodiment 268, wherein at least three of $H^{a2}$, $H^{b2}$, $H^{c2}$, $H^{d2}$, and $H^{e2}$ are each independently a population of isotopes of hydrogen that is at least 5% deuterium.

Embodiment 271. The pharmaceutical composition of embodiment 269, wherein each of $H^{a2}$, $H^{b2}$, $H^{c2}$, $H^{d2}$, and $H^{e2}$ is independently a population of isotopes of hydrogen that is at least 5% deuterium.

Embodiment 272. The pharmaceutical composition of embodiment 270, wherein at least three of $H^{a2}$, $H^{b2}$, $H^{c2}$, $H^{d2}$, and $H^{e2}$ are each independently a population of isotopes of hydrogen that is at least 50% deuterium.

Embodiment 273. The pharmaceutical composition of embodiment 271, wherein each of $H^{a2}$, $H^{b2}$, $H^{c2}$, $H^{d2}$, and $H^{e2}$ is independently a population of isotopes of hydrogen that is at least 50% deuterium.

Embodiment 274. The pharmaceutical composition of embodiment 272, wherein at least three of $H^{a2}$, $H^{b2}$, $H^{c2}$, $H^{d2}$, and $H^{e2}$ are each independently a population of isotopes of hydrogen that is at least 95% deuterium.

Embodiment 275. The pharmaceutical composition of embodiment 273, wherein each of $H^{a2}$, $H^{b2}$, $H^{c2}$, $H^{d2}$, and $H^{e2}$ is independently a population of isotopes of hydrogen that is at least 95% deuterium.

Embodiment 276. The pharmaceutical composition of any one of embodiments 227-275, further comprising a source of magnesium.

Embodiment 277. The pharmaceutical composition of any one of embodiments 227-276, further comprising magnesium chloride.

Embodiment 278. The pharmaceutical composition of any one of embodiments 227-277, further comprising vitamin D.

Embodiment 279. The pharmaceutical composition of any one of embodiments 227-278, wherein the pharmaceutical composition is an oral form.

Embodiment 280. The pharmaceutical composition of any one of embodiments 227-279, wherein the pharmaceutical composition is a tablet.

Embodiment 281. A method of treating a condition in a subject in need thereof, the method comprising administering to the subject a therapeutically effective amount of the pharmaceutical composition of any one of embodiments 1-280.

Embodiment 282. A method for preventing or delaying the onset of a condition in a subject in need thereof, the method comprising administering to the subject a therapeutically effective amount of the pharmaceutical composition of any one of embodiments 1-280.

Embodiment 283. A method of reducing a likelihood of developing a condition in a subject in need thereof, the method comprising administering to the subject a therapeutically effective amount of the pharmaceutical composition of any one of embodiments 1-280.

Embodiment 284. The method of any one of embodiments 281-283, wherein the condition is psoriasis.

What is claimed is:

1. A pharmaceutical composition comprising:
a) an amount of at least 1 mg of:
$(C(H^{a1})(H^{b1})(H^{c1}))$—$(C(H^{d1})(H^{e1}))$—$(C(H^{f1})(H^{g1}))$—COOH or a pharmaceutically-acceptable salt thereof, wherein:
$H^{a1}$ is a population of isotopes of hydrogen that is about a natural abundance of isotopes of hydrogen or a population of isotopes of hydrogen that is at least 1% deuterium;
$H^{b1}$ is a population of isotopes of hydrogen that is about a natural abundance of isotopes of hydrogen or a population of isotopes of hydrogen that is at least 1% deuterium;
$H^{c1}$ is a population of isotopes of hydrogen that is about a natural abundance of isotopes of hydrogen or a population of isotopes of hydrogen that is at least 1% deuterium;
$H^{d1}$ is a population of isotopes of hydrogen that is about a natural abundance of isotopes of hydrogen or a population of isotopes of hydrogen that is at least 1% deuterium;
$H^{e1}$ is a population of isotopes of hydrogen that is about a natural abundance of isotopes of hydrogen or a population of isotopes of hydrogen that is at least 1% deuterium;
$H^{f1}$ is a population of isotopes of hydrogen that is about a natural abundance of isotopes of hydrogen or a population of isotopes of hydrogen that is at least 1% deuterium; and $H^{g1}$ is a population of isotopes of hydrogen that is about a natural abundance of isotopes of hydrogen or a population of isotopes of hydrogen that is at least 1% deuterium, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 1% deuterium; and b) a solid pharmaceutically-acceptable excipient.

2. The pharmaceutical composition of claim 1, wherein the amount of butyric acid or the pharmaceutically-acceptable salt thereof is at least 10 mg.

3. The pharmaceutical composition of claim 1, wherein the amount of butyric acid or the pharmaceutically-acceptable salt thereof is at least 100 mg.

4. The pharmaceutical composition of claim 1, wherein the amount of butyric acid or the pharmaceutically-acceptable salt thereof is at least 800 mg.

5. The pharmaceutical composition of claim 1, the pharmaceutical composition comprising the pharmaceutically-acceptable salt of butyric acid, wherein the pharmaceutically-acceptable salt is sodium butyrate.

6. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 5% deuterium.

7. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 10% deuterium.

8. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 25% deuterium.

9. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 50% deuterium.

10. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 75% deuterium.

11. The pharmaceutical composition of claim 1, wherein at least one of $H^{a1}$, $H^{b1}$, $H^{c1}$, $H^{d1}$, $H^{e1}$, $H^{f1}$, and $H^{g1}$ is a population of isotopes of hydrogen that is at least 80% deuterium, at least 85% deuterium, at least 90% deuterium, at least 95% deuterium, at least 99% deuterium.

12. The pharmaceutical composition of claim 1, wherein at least five of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium, at least 5% deuterium, at least 50% deuterium, or at least 95% deuterium.

13. The pharmaceutical composition of claim 1, wherein each of $H^{a1}$, $H^{b1}$, $H^{c1}$, $H^{d1}$, $H^{e1}$, $H^{f1}$, and $H^{g1}$ is independently a population of isotopes of hydrogen that is at least 1% deuterium, at least 5% deuterium, at least 50% deuterium, or at least 95% deuterium.

14. The pharmaceutical composition of claim 1, wherein at least three of $H^{a1}$, $H^{b1}$, $H^{c1}$, $H^{d1}$, $H^{e1}$, $H^{f1}$, and $H^{g1}$ are each independently a population of isotopes of hydrogen that is at least 1% deuterium, at least 5% deuterium, at least 50% deuterium, or at least 95% deuterium.

15. The pharmaceutical composition of claim 1, wherein the solid pharmaceutically-acceptable excipient is a tablet filler.

16. The pharmaceutical composition of claim 1, wherein the pharmaceutical composition is an oral form.

17. The pharmaceutical composition of claim 1, wherein the pharmaceutical composition is a tablet.

18. The pharmaceutical composition of claim 1, further comprising a source of magnesium.

19. The pharmaceutical composition of claim 1, further comprising magnesium chloride.

20. The pharmaceutical composition of claim 1, further comprising vitamin D.

* * * * *